(12) United States Patent
Parhami

(10) Patent No.: US 7,897,588 B2
(45) Date of Patent: Mar. 1, 2011

(54) AGENTS AND METHODS FOR ENHANCING BONE FORMATION

(75) Inventor: Farhad Parhami, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 763 days.

(21) Appl. No.: 10/524,945

(22) PCT Filed: Aug. 28, 2003

(86) PCT No.: PCT/US03/27105
§ 371 (c)(1),
(2), (4) Date: Feb. 16, 2005

(87) PCT Pub. No.: WO2004/019884
PCT Pub. Date: Mar. 11, 2004

(65) Prior Publication Data
US 2006/0270645 A1     Nov. 30, 2006

(51) Int. Cl.
*A61K 31/56*     (2006.01)
*A01N 63/00*     (2006.01)

(52) U.S. Cl. .................................. 514/182; 424/93.7

(58) Field of Classification Search .................. 514/182, 514/824; 435/6, 11, 91.2
See application file for complete search history.

(56) References Cited

U.S. PATENT DOCUMENTS

| | | | |
|---|---|---|---|
| 3,887,545 | A | 6/1975 | Iacobelli et al. |
| 4,183,852 | A | 1/1980 | Kaiser |
| 4,743,597 | A | 5/1988 | Javitt et al. |
| 5,929,062 | A | 7/1999 | Haines |
| 6,080,779 | A | 6/2000 | Gasper et al. |
| 6,184,215 | B1 | 2/2001 | Elias et al. |
| 6,586,189 | B2 | 7/2003 | Forman |
| 6,893,830 | B1 | 5/2005 | Janowski et al. |
| 2003/0153541 | A1 | 8/2003 | Dudley et al. |
| 2004/0176423 | A1* | 9/2004 | Paralkar .................. 514/345 |
| 2004/0235739 | A1 | 11/2004 | Mahanthappa |
| 2005/0095677 | A1 | 5/2005 | Liu et al. |
| 2006/0270645 | A1 | 11/2006 | Parhami |

FOREIGN PATENT DOCUMENTS

| | | |
|---|---|---|
| GB | 2 320 190 | 6/1998 |
| WO | WO 97/40137 | 10/1997 |
| WO | WO 00/54759 | 9/2000 |
| WO | WO 01/15676 | 3/2001 |
| WO | WO 02/080952 | 10/2002 |
| WO | WO 2004/019884 A2 | 3/2004 |
| WO | WO 2005/028616 | 3/2005 |
| WO | WO/2005/020928 | 10/2005 |
| WO | WO/2006/012902 | 9/2006 |
| WO | WO 2006/110490 | 10/2006 |
| WO | WO/2007/098281 | 1/2007 |
| WO | WO 2007/028101 | 3/2007 |
| WO | WO 2008/041003 A2 | 4/2008 |
| WO | WO 2008/115469 | 9/2008 |

OTHER PUBLICATIONS

Larsson et al. "Kinetics of G1 progression in 3T6 and SV-3T3 cells following treatment by 25-hydroxycholesterol." Cancer Res. Mar. 1986;46(3):1233-8.*
Parish et al., Side-chain oxysterol regulation of 3-Hydroxy-3-methylglutaryl Coenzyme A reductase activity, 1995, Lipids, pp. 247-251.*
Wang et al., The Nicolas Andry award. The pathogenesis and prevention of steroid-induced osteonecrosis. Clin Orthop Relat Res. Jan. 2000;(370):295-310.*
Garret et al., The role of statins as potential targets for bone formation. Arthritis Research, 2002, pp. 237-240.*
International Search Report issued in PCT Application No. PCT/US07/05073, mailed on Oct. 29, 2007.
Written Opinion issued in PCT Application No. PCT/US07/05073, mailed on Oct. 29, 2007.
Nagano et al., Chemistry and Biochemistry of Chinese Drugs. Part II. Hydroxylated Sterols, Cytotoxic toward Cancerous Cells: Synthesis and Testing. J. Chem. Research, Apr. 1977, M, pp. 2522-2571, (With English Language Synopsis).
Wiersig et al., Stereospecific Synthesis of the Side Chain of the Steroidal Plant Sex Hormone Oogoniol. J. Org. Chem., (1979) vol. 44, No. 19, pp. 3374-3382.
Makino et al., Steroid Conformations in Solid and Solution: Stereoselectivity of Grignard Addition to 20-Keto Steroids, J. Org. Chem., (1978) vol. 43, No. 2, pp. 276-280.
Int'l Search Report for PCT/US03/27105, Mailed May 5, 2004.
Int'l Search Report for PCT/US04/28162, Mailed Feb. 22, 2005.
Hanada et al., Stimulatory Effects of Basic Fibroblast Growth Factor and Bone Morphogenetic Protein-2 Osteogenic Differentiation of Rat Bone Marrow-Derived Mesenchymal Stem Cells, J. Bone and Mineral Res. Oct. 1997, vol. 12, No. 10, pp. 1606-1614.
Thies et al., Recombinant Human Bone Morphogenetic Protein-2 Induces Osteoblastic Differentiation in W-20-17 Stromal Cells, Endocrinology 1992, vol. 130, No. 3, pp. 1318-1324. Sammons et al., The Role of BMP-6, IL-6 and BMP-4 in Mesenchymal Stem Cell-Dependent Bone Development: Effects on Osteoblastic Differentiation Induced by Parathyroid Hormone and Vitamin D3, Jun. 2004, Stem Cells and Development vol. 13, pp. 273-280.
Aghaloo TL, Amantea CM, Cowan CM, Richardson JA, Wu BM, Parhami F, Tetradis S. Oxysterols enhance osteoblast differentiation in vitro and bone healing in vivo. J Orthop Res. Nov. 2007;25(11):1488-97 (also known as Aghaloo 2006 in press).
Akazawa C, Isuzuki H, Nakamura Y, Sasaki Y, Ohsaki K, Nakamura S, arakawa Y, Kohsaka S. The upregulated expression of sonic hedgehog in motor neurons after rat facial nerve axotomy. J Neuroscience 2004; 24:7923-7930.

(Continued)

*Primary Examiner* — Maria Leavitt
(74) *Attorney, Agent, or Firm* — Venable LLP; Nancy J. Axelrod; Michael A. Gollin

(57) ABSTRACT

The present invention discloses agents and methods for inducing osteoblastic cellular differentiation, as well as the use of such agents and method to treat patients to maintain bone mass, enhance bone formation and/or bone repair. Exemplary agents include oxysterols, alone or in combination with particular oxysterols, or other agents known to assist in bone formation. The invention further includes medicaments including oxysterols for the treatment of bone disorders, local injections of oxysterols or cells (206) and implants (202) having agents or cells (203) to facilitate bone repair.

10 Claims, 12 Drawing Sheets

OTHER PUBLICATIONS

Almeida M, Han L, Bellido T, Manolagas SC, Kousteni S. Wnt proteins prevent apoptosis of both uncommitted osteoblast progenitors and differentiated osteoblasts by beta-catenin-dependent and -independent signaling cascades involving Src/ERK and phosphatidylinositol 3-kinase/AKT. J Biol Chem. Dec. 16, 2005;280(50):41342-51.

Amantea CM et al. 2006, Oxysterols are novel activators of hedgehog and Wnt signaling, J Bone Miner Res 21:SI;S156.

Banerjee C, McCabe LR, Choi JY, Hiebert SW, Stein JL, Stein GS, Lian JB. Runt homology domain proteins in osteoblast differentiation: AML3/CBFA1 is a major component of a bone-specific complex. J Cell Biochem. Jul. 1, 1997;66(1):1-8.

Bannai K, Morisaki M, Ikekawa N. Studies on steroids. Part 37. Synthesis of the four stereoisomers of 20,22-epoxycholesterol. J Chem Soc Perkins Trans 1 1979; 2116-2120.

Basu S, Michaëlsson K, Olofsson H, Johansson S, Melhus H. Association between oxidative stress and bone mineral density. Biochem Biophys Res Commun. Oct. 19, 2001;288(1):275-9.

Beckers L, Heeneman S, Wang L, Burkly LC, Rousch MM, Davidson NO, Gijbels MJ, de Winther MP, Daemen MJ, Lutgens E. Disruption of hedgehog signalling in ApoE -/- mice reduces plasma lipid levels, but increases atherosclerosis due to enhanced lipid uptake by macrophages. J Pathol. Aug. 2007;212(4):420-8.

Bennett CN, Longo KA, Wright WS, Suva LJ, Lane TF, Hankenson KD, MacDougald OA. Regulation of osteoblastogenesis and bone mass by Wnt10b. Proc Natl Acad Sci U S A. Mar. 1, 2005;102(9):3324-9.

Bennett CN, Ross SE, Longo KA, Bajnok L, Hemati N, Johnson KW, Harrison SD, MacDougald OA. Regulation of Wnt signaling during adipogenesis. J Biol Chem. Aug. 23, 2002;277(34):30998-1004.

Bergman RJ, Gazit D, Kahn AJ, Gruber H, McDougall S, Hahn TJ. Age-related changes in osteogenic stem cells in mice. J Bone Miner Res 1996; 11:568-577.

Bestmann HJ, Soliman FM. Synthesis and reaction of diazoacetyl chloride. Angew Chem 1979; 91:1012-1013.

Bijlsma MF, Peppelenbosch MP, Spek A. Hedgehog morphogen in cardiovascular disease. Circulation 114:1985-1991; 2006.

Bijlsma MF, Spek CA, Peppelenbosch MP. Hedgehog: an unusual signal transducer. BioEssays 26:387-394; 2004.

Bilezikian JP, Kurland ES. Therapy of male osteoporosis with parathyroid hormone. Calcif Tissue Int 2001; 69:248-251.

Bjorkhem I, Diczfalusy U. Oxysterols: friends, foes, or just fellow passengers? Arterioscler Thromb Vasc Biol 22:734-742; 2002.

Bjorkhem I, Meaney S, Diczfalusy U. Oxysterols in human circulation: which role do they play? Curr Opion Lipidol 13:247-253; 2002.

Bjorkhem I, Reihner E, Angelin B, Ewerth S, Akerlund J, Einarsson K. On the possible use of the serum level of $7\alpha$-hydroxycholesterol as a marker for incrased activity of the cholesterol $7\alpha$-hydroxylase in humans. J Lipid Res 1987; 28:889-894.

Boguslawski G, Hale LV, Yu XP, Miles RR, Onyia JE, Santerre RF, Chandrasekhar S. Activation of osteocalcin transcription involves interaction of protein kinase A- and protein kinase C-dependent pathways. J Biol Chem. Jan. 14, 2000;275(2):999-1006.

Boland GM, Perkins G, Hall DJ, Tuan RS. Wnt 3a promotes proliferation and suppresses osteogenic differentiation of adult human mesenchymal stem cells. J Cell Biochem. Dec. 15, 2004;93(6):1210-30.

Braunersreuther V, Mach F. Leukocyte recruitment in atherosclerosis: potential targets for therapeutic approaches? Cell Mol Life Sci 63:2079-2088; 2006.

Bunta W, Yoshiaki N, Takehiko O, Hisashi M. Steroids 2004, 69: 483-493.

Burger A, Colobert F, Hetru C, Luu B. Tetrahedron 1988, 44: 1141-1152.

Byon C, Gut M. Stereospecific synthesis of the four 20,22-epoxycholesterols and of (Z)-20(22)-Dehydrocholesterol. J Org Chem 1976; 41:3716-3722.

Byrd N, Grabel L. Hedgehog signaling in murine vasculogenesis and angiogenesis. Trends Cardiovasc Med 14:308-313; 2004.

Cadot C, Poirier D, Philip A. Tetrahedron 2006, 62: 4384-4392.

Caplan AI, Bruder SP. Mesenchymal stem cells: building blocks for molecular medicine in the 21st century. Trends Mol Med. Jun. 2001;7(6): 259-64. Review.

Caplan AI. The mesengenic process. Bone Repair and Regeneration 1994; 21:429-435.

Chan GK, Duque G. Age-related bone loss: old bone, new facts. Gerontology 2002; 48:62-71.

Chaudhuri NK, Williams IG, Nickolson R, Gut M. Stereochemistry of the addition reactions of Grignard reagents to 20-keto steroids. Syntheses of $17\alpha,20\alpha$-dihydroxycholesterol. J Org Chem 1969; 34:3759-3766.

Chen D, Zhao M, Mundy GR. Bone morphogenetic proteins. Growth Factors. Dec. 2004;22(4):233-41. Review.

Chen JK, Iaipale J, Cooper MK, Beachy PA. Inhibition of hedgehog signaling by direct binding of cyclopamine to Smoothened. Genes & Develop 2002; 16:2743-2748.

Chen XD, Shi S, Xu T, Robey PG, Young MF. Age-related osteoporosis in biglycan-deficient mice is related to defects in bone marrow stromal cells. J Bone Miner Res. Feb. 2002;17(2):331-40.

Chuu CP, Chen RY, Hiipakka RA, Kokontis JM, Warner KV, Xiang J, Liao S. The liver X receptor agonist T0901317 acts as androgen receptor antagonist in human prostate cancer cells. Biochem Biophys Res Commun. Jun. 1, 2007;357(2):341-6. Epub Mar. 28, 2007.

Chuu CP, Hiipakka RA, Kokontis JM, Fukuchi J, Chen RY, Liao S. Inhibition of tumor growth and progression of LNCaP prostate cancer cells in athymic mice by androgen and liver X receptor agonist. Cancer Res. Jul. 1, 2006;66(13):6482-6.

Clément-Lacroix P, Ai M, Morvan F, Roman-Roman S, Vayssière B, Belleville C, Estrera K, Warman ML, Baron R, Rawadi G. Lrp5-independent activation of Wnt signaling by lithium chloride increases bone formation and bone mass in mice. Proc Natl Acad Sci U S A. Nov. 29, 2005;102(48):17406-11.

Clevers H. Wnt/beta-catenin signaling in development and disease. Cell. Nov. 3, 2006;127(3):469-80. Review.

Cohen MM. The hedgehog signaling network. Am J Med Gen 2003; 123A:5-28.

Cummings SR, Melton LJ. Epidemiology and outcomes of osteoporotic fractures. Lancet. May 18, 2002;359(9319):1761-7. Review.

Day TF, Guo X, Garrett-Beal L, Yang Y. Wnt/beta-catenin signaling in mesenchymal progenitors controls osteoblast and chondrocyte differentiation during vertebrate skeletogenesis. Dev Cell. May 2005;8(5):739-50.

de la Rosa MA, Velarde E, Guzman A. Synthetic Commun. 1990, 20: 2059-2064.

Debiais F, Lefevre G, Lemonnier J, Le Mée S, Lasmoles F, Mascarelli F, Marie PJ. Fibroblast growth factor-2 induces osteoblast survival through a phosphatidylinositol 3-kinase-dependent, -beta-catenin-independent signaling pathway. Exp Cell Res. Jul. 1, 2004;297(1):235-46.

Devos A, Remion J, Frisque-Hesbain AM, Colens A, Ghosez L. Syntheseis of acyl halides under very mild conditions. J Chem soc Chem Commun 1979; 1180-1181.

Drew J, Letellier M, Morand P, Szabo AG. J of Org. Chem 1987, 52: 4047-4052 (no detailed info found in PubMed).

Ducy P, Zhang R, Geoffroy V, Ridall AL, Karsenty G. Osf2/Cbfal: A transcriptional activator of osteoblast differentiation. Cell 1997; 89:747-754.

Ducy P. Cbfal : a molecular switch in osteoblast biology. Dev Dyn. Dec. 2000;219(4):461-71.

Dwyer JR, Sever N, Carlson M, Nelson SF, Beachy PA, Parhami F. Oxysterols are novel activators of the hedgehog signaling pathway in pluripotent mesenchymal cells. J Biol Chem 2007, 282: 8956-8968.

Eastell R. Treatment of postmenopausal osteoporosis. New Eng J Med 1998; 338(11):736-746.

Edwards PA, Ericsson J. Sterols and isoprenoids: signaling molecules derived from the cholesterol biosynthetic pathway. Annu Rev Biochem 68:157-185; 1999.

Edwards PA, Kast HR, Anisfeld AM. BAREing it all: the adoption of LXR and FXR and their roles in lipid metabolism. J Lipid Res 2002; 43:2-12.

Ettinger MP. Aging bone and osteoporosis: strategies for preventing fractures in the elderly. Arch Intern Med. Oct. 13, 2003;163(18):2237-46. Review.

Fajas L, Schoonjans K, Gelman L, Kim JB, Najib J, Martin G, Fruchart JC, Briggs M, Spiegelman BM, Auwerx J. Regulation of peroxisome proliferator-activated receptor gamma expression by adipocyte differentiation and determination factor 1/sterol regulatory element binding protein 1: implications for adipocyte differentiation and metabolism. Mol Cell Biol. Aug. 1999;19(8):5495-503.

Franceschi RT, Wang D, Krebsbach PH, Rutherford RB. Gene therapy for bone formation: in vitro and in vivo osteogenic activity of an adenovirus expressing BMP7. J Cell Biochem. Jun. 6, 2000;78(3):476-86.

Franceschi RT, Xiao G. Regulation of the osteoblast-specific transcription factor, Runx2: responsiveness to multiple signal transduction pathways. J Cell Biochem. Feb. 15, 2003;88(3):446-54. Review.

Fujita T, Azuma Y, Fukuyama R, Hattori Y, Yoshida C, Koida M, Ogita K, Komori T. Runx2 induces osteoblast and chondrocyte differentiation and enhances their migration by coupling with P13K-Akt signaling. J Cell Biol. Jul. 5, 2004;166(1):85-95. Epub Jun. 28, 2004.

Fukuchi J, Kokontis JM, Hiipakka RA, Chuu CP, Liao S. Antiproliferative effect of liver X receptor agonists on LNCaP human prostate cancer cells. Cancer Res. Nov. 1, 2004;64(21):7686-9.

Garrett IR, Chen D, Gutierrez G, Zhao M, Escobedo A, Rossini G, Harris SE, Gallwitz W, Kim KB, Hu S, Crews CM, Mundy GR. Selective inhibitors of the osteoblast proteasome stimulate bone formation in vivo and in vitro. J Clin Invest. Jun. 2003;111(11):1771-82.

Gaur T, Lengner CJ, Hovhannisyan H, Bhat RA, Bodine PV, Komm BS, Javed A, van Wijnen AJ, Stein JL, Stein GS, Lian JB. Canonical WNT signaling promotes osteogenesis by directly stimulating Runx2 gene expression. J Biol Chem. Sep. 30, 2005;280(39):33132-40. Epub Jul. 25, 2005.

Gen AVD, Wiedhaup K, Swoboda JJ, Dunathan HC, Johnson WS. J Am Chem Soc 1973, 95: 2656-2663.

Ghosh-Choudhury N, Abboud SL, Nishimura R, Celeste A, Mahimainathan L, Choudhury GG. Requirement of BMP-2-induced phosphatidylinositol 3-kinase and Akt serine/threonine kinase in osteoblast differentiation and Smad-dependent BMP-2 gene transcription. J Biol Chem. Sep. 6, 2002;277(36):33361-8. Epub Jun. 25, 2002. Erratum in: J Biol Chem. May 2, 2003;278(18):16452.

Ghosh-Choudhury N, Mandal CC, Choudhury GG. Statin-induced Ras activation integrates the phosphatidylinositol 3-kinase signal to Akt and MAPK for bone morphogenetic protein-2 expression in osteoblast differentiation. J Biol Chem. Feb. 16, 2007;282(7):4983-93.

Gimble JM, Robinson Covered Entity, Wu X, Kelly KA, Rodriguez BR, Kliewer SA, Lehmann JM, Morris DC. Peroxisome proliferator-activated receptor-γ activation by thiazolidinediones induces adipogenesis in bone marrow stromal cells. Mol Pharmacol 1996; 50:1087-1094.

Goltzman D. Discoveries, drugs and skeletal disorders. Nat Rev Drug Discov. Oct. 2002;1(10):784-96.

Gordon MD, Nusse R. Wnt signaling: multiple pathways, multiple receptors, and multiple transcription factors. J Biol Chem. Aug. 11, 2006;281(32):22429-33. Epub Jun. 22, 2006. Review.

Gori F, Thomas T, Hicok KC, Spelsberg TC, Riggs BL. Differentiation of human marrow stromal precursor cells: bone morphogenetic protein-2 increases OSF2/CBFA1, enhances osteoblast commitment, and inhibits late adipocyte maturation. J Bone Miner Res. Sep. 1999;14(9):1522-35.

Hanley K, Ng DC, He SS, Lau P, Min K, Elias PM, Bikle DD, Mangelsdorf DJ, Williams ML, Feingold KR. Oxysterols induce differentiation in human keratinocytes and increase AP-1-dependent involucrin transcription. J Invest Dermatol 2000; 114:545-553.

Hayden JM, Brachova L, Higgins K, Obermiller L, Sevanian A, Khandrika S, Reaven PD. Induction of moncyte differentiation and foam cell formation in vitro by 7-ketocholesterol. J Lipid Res 2002; 43:26-35.

Hicok KC, Thomas T, Gori F, Rickard DJ, Spelsberg TC, Riggs BL. Development and characterization of conditionally immortalized osteoblast precursor cell lines from human bone marrow stroma. J Bone Miner Res 1998; 13(2):205-2217.

Hill TP, Später D, Taketo MM, Birchmeier W, Hartmann C. Canonical Wnt/beta-catenin signaling prevents osteoblasts from differentiating into chondrocytes. Dev Cell. May 2005;8(5):727-38.

Honda M, Komori T. Biologically active glycosides from Asteroidia. XI. Structures of thornasterols A and B. Tetrahedron Lett 1986; 27:3396-3372.

Honda T, Katoh M, Yamane S. J Chem Soc., Perkin Trans. 1996, 1: 2291-2296 (no detailed info found in PubMed).

Hosack DA, Dennis G Jr, Sherman BT, Lane HC, Lempicki RA. Identifying biological themes within lists of genes with EASE. Genome Biol. 2003;4(10):R70. Epub Sep. 11, 2003.

Hu H, Hilton MJ, Tu X, Yu K, Ornitz DM, Long F. Sequential roles of hedgehog and Wnt signaling in osteoblast development. Development 132:49-60; 2004.

Ichioka N, Inaba M, Kushida T, Esumi T, Takahara K, Inaba K, Ogawa R, Iida H, Ikehara S. Prevention of senile osteoporosis in SAMP6 mice by intrabone marrow injection of allogeneic bone marrow cells. Stem Cells. 2002;20(6):542-51.

Iwata H, Sakano S, Itoh T, Bauer TW. Demineralized bone matrix and native bone morphogenetic protein in orthopaedic surgery. Clin Orthop Relat Res. Feb. 2002;(395):99-109. Review.

Johnson ML, Harnish K, Nusse R, Van Hul W. LRP5 and Wnt signaling: a union made for bone. J Bone Miner Res. Nov. 2004;19(11):1749-57.

Jung ME, Johnson TW. First total synthesis of Zestobergesterol A and active structural analogues of the Zestobergesterol. Organic Lett 1999; 1:1671-1674.

Juvet LK, Andresen SM, Schuster GU, Dalen KT, Tobin KA, Hollung K, Haugen F, Jacinto S, Ulven SM, Bamberg K, Gustafsson JA, Nebb HI. On the role of liver X receptors in lipid accumulation in adipocytes. Mol Endocrinol. Feb. 2003;17(2):172-82.

Kametani T, Tsubuki M, Higurashi K, Honda T. J Org Chem 1986, 51: 2932-2939.

Kennell JA, MacDougald OA. Wnt signaling inhibits adipogenesis through beta-catenin-dependent and -independent mechanisms. J Biol Chem. Jun. 24, 2005;280(25):24004-10.

Kha HT, Basseri B, Shouhed D, Richardson J, Tetradis S, Hahn TJ, Parhami F. Oxysterols regulate differentiation of mesenchymal stem cells: pro-bone and anti-fat. J Bone Miner Res 19:830-840; 2004.

Kim JB, Wright HM, Wright M, Spiegelman BM. ADD1/SREBP1 activates PPARgamma through the production of endogenous ligand. Proc Natl Acad Sci U S A. Apr. 14, 1998;95(8):4333-7.

Kim WK, Meliton V, Amantea CM, Hahn TJ, Parhami F. 20(S)-hydroxycholesterol inhibits PPARgamma expression and adipogenic differentiation of bone marrow stromal cells through a hedgehog-dependent mechanism. J Bone Miner Res. Nov. 2007;22(11):1711-9.

Komori T. Regulation of skeletal development by the Runx family of transcription factors. J Cell Biochem. Jun. 1, 2005;95(3):445-53.

Kurland ES, Cosman F, McMahon DJ, Rosen CJ, Lindsay R, Bilezikian J. Parathyroid hormone as a therapy for idiopathic osteoporosis in men: effects on bone mineral density and bone markers. J Clin Endocrinol Metab 2000; 85:3069-3076.

Lehmann IM, Kliewer SA, Moore LB, Smith-Oliver TA, Oliver BB, Su J, Sundseth SS, Winegar DA, Blanchard DE, Spencer TA, Willson TM. Activation of the nuclear receptor LXR by oxysterols defines a new hormone response pathway. J Biol Chem 1997; 272:3137-3140.

Li RH, Wozney JM. Delivering on the promise of bone morphogenetic proteins. Trends Biotechnol. Jul. 2001;19(7):255-65. Review.

Libby P. Inflammation in atherosclerosis. Nature 420:868-874; 2002.

Lieberman JR, Daluiski A, Einhorn TA. The role of growth factors in the repair of bone. J Bone & Joint Surg 2002; 84A:1032-1044.

Long F, Zhang XM, Karp S, Yang Y, McMahon AP. Genetic manipulation of hedgehog signaling in the endochondral skeleton reveals a direct role in the regulation of chondrocyte proliferation. Development 2001; 128:5099-5108.

Lum L, Beachy PA. The hedgehog response network: sensors, switches, and routers. Science 304:1755-1759; 2004.

Maeda T, Matsunuma A, Kawane T, Horiuchi N. Simvastatin promotes osteoblast differentiation and mineralization in MC3T3-E1 cells. Biochem Biophys Res Commun. Jan. 26, 2001;280(3):874-7.

Maggio D, Barabani M, Pierandrei M, Polidori MC, Catani M, Mecocci P, Senin U, Pacifici R, Cherubini A. Marked decrease in plasma antioxidants in aged osteoporotic women: results of a cross-sectional study. J Clin Endocrinol Metab. Apr. 2003;88(4):1523-7.

Majors AK, Boehm CA, Nitto H, Midura RJ, Muschler GF. Characterization of human bone marrow stromal cells with respect to osteoblastic differentiation. J Bone & Joint Surgery 1997; 15:546-557.

Manolagas SC. Cellular and molecular mechanisms of osteoporosis. Aging 1998; 10(3):182-190.

Manolagas SC. Birth and death of bone cells: basic regulatory mechanisms and implications for the pathogenesis and treatment of osteoporosis. Endocr Rev. Apr. 2000;21(2):115-37.

Mazzocchi PH, Wilson FK, Klinger L, Miniamikawa S. J Org Chem 1983, 48: 2981-2989 (no detailed info found in PubMed).

Mbalaviele G, Sheikh S, Stains JP, Salazar VS, Cheng SL, Chen D, Civitelli R. Beta-catenin and BMP-2 synergize to promote osteoblast differentiation and new bone formation. J Cell Biochem. Feb. 1, 2005;94(2):403-18.

Meaney S, Hassan M, Sakinis A, Lutjohann D, von Bergmann K, Wennmalm A, Diczfalusy U, Bjorkhem I. Evidence that the major oxysterols in human circulation originate from distinct pools of cholesterol: a stable isotope study. J Lipid Res 2001; 42:70-78.

Melton LI. How many women have osteoporosis now? J Bone Miner Res 1995; 10:175-177.

Meunier P, Aaron J, Edouard C, Vignon G. Osteoporosis and the replacement of cell populations of the marrow by adipose tissue: A quantitative study of 84 iliac bone biopsies. Clinical Orthopedics and Related Res 1971; 80:147-154.

Mitsunobu O. The use of diethyl azodicarboxylate and triphenylphosphine in syntheses and transformation of natural products. Synthesis 1981; 1-28.

Miyamoto K, Suzuki H, Yamamoto S, Saitoh Y, Ochiai E, Moritani S, Yokogawa K, Waki Y, Kasugai S, Sawanishi H, Yamagami H. Prostaglandin E2-mediated anabolic effect of a novel inhibitor of phosphodiesterase 4, XT-611, in the in vitro bone marrow culture. J Bone Miner Res. Aug. 2003;18(8):1471-7.

Mody N, Parhami F, Sarafian TA, Demer LL. Oxidative stress modulates osteoblastic differentiation of vascular and bone cells. Free Radic Biol Med. Aug. 15, 2001;31(4):509-19.

Moerman EJ, Teng K, Lipschitz DA, Lecka-Czernik B. Aging activates adipogenic and suppresses osteogenic programs in mesenchymal marrow stroma/stem cells: the role of PPAR-gamma2 transcription factor and TGF-beta/BMP signaling pathways. Aging Cell. Dec. 2004;3(6):379-89.

Morisaki M, Sato S, Ikekawa N. Studies on steroids. XLV. Synthesis of the four stereoisomers of 20,22-dihydroxycholesterol. Chem Pharm Bull 1977; 25:2576-2583.

Mullor JL, Dahmane N, Sun T, Ruiz i Altaba A. Wnt signals are targets and mediators of Gli function. Curr Biol. May 15, 2001;11(10):769-73.

Mullor JL, Sanchez P, Altaba AR. Pathways and consequences: hedgehog signaling in human disease. Trends Cell Bio 2002; 12:562-569.

Mundy GR. Directions of drug discovery in osteoporosis. Annu Rev Med 2002; 53;337-354.

Olkkonen VM, Lehto M. Oxysterols and oxysterol binding proteins: role in lipid metabolism and atherosclerosis. Ann Med 36:562-572; 2004.

Otto F, Thronell AP, Crompton T, Denzel A, Gilmour KC, Rosewell IR, Stamp GWH, Beddington RSP, Mundlos S, Olsen BR, Selby PB, Owen MJ. Cbfa1, a candidate gene for cleidocranial dysplasia syndrome, is essential for osteoblast differentiation and bone development. Cell 1997; 89:765-771.

Panakova D, Sprong H, Marois E, Thiele C, Eaton S. Lipoprotein particles are required for hedgehog and wingless signaling. Nature 435:58-65; 2005.

Parhami F, Mody N, Gharavi N, Ballard AJ, Tintut Y, Demer LL. Role of the cholesterol biosynthetic pathway in osteoblastic differentiation of marrow stromal cells. J Bone Miner Res. Nov. 2002;17(11):1997-2003.

Peet DJ, Janowski BA, Mangelsdorf DJ. The LXRs: a new class of oxysterol receptors. Curr Opin Genetics & Develop 1998; 8:571-575.

Pittenger MF, Mackay AM, Beck SC, Jaiswal RK, Douglas R, Mosca JD, Moorman MA, Simonetti DW, Craig S, Marshak DR. Multilineage potential of adult human mesenchymal stem cells. Science 1999; 284:143-147.

Poza J, Rega M, Paz V, Alonso B, Rodriguez J, Salvador N, Fernández A, Jiménez C. Synthesis and evaluation of new 6-hydroximinosteroid analogs as cytotoxic agents. Bioorg Med Chem. Jul. 15, 2007;15(14):4722-40.

Prockop DJ. Marrow stromal cells as stem cells for nonhematopoietic tissues. Science 1997; 276:71-74.

Quarto R, Thomas D, Liang CT. Bone progenitor cell deficits and the age-associated decline in bone repair capacity. Calcif Tissue Int. Feb. 1995;56(2):123-9.

Raisz LG. The osteoporosis revolution. Ann Int Med 1997; 126:458-462.

Rao AS. Addition reactions with formation of carbon-oxygen bones: (1) General methods of epoxidation. Comprehensive Organic Synthesis, Pergamon Press, Eds. Trost BM, Fleming I. 1991; 7 (chapter 3.1); 376-380.

Rawadi G, Vayssière B, Dunn F, Baron R, Roman-Roman S. BMP-2 controls alkaline phosphatase expression and osteoblast mineralization by a Wnt autocrine loop. J Bone Miner Res. Oct. 2003; 18(10):1842-53.

Reeve J, Mitchell A, Tellez M, Hulme P, Green JR, Wardley-Smith B, Mitchell R. Treatment with parathyroid peptides and estrogen replacement for severe postmenopausal vertebral osteoporosis: prediction of long-term responses in spine and femur. J Bone Miner Res 2001; 19:102-114.

Reinholz GG, Getz B, Pederson L, Sanders ES, Subramaniam M, Ingle JN, Spelsberg TC. Bisphosphonates directly regulate cell proliferation, differentiation, and gene expression in human osteoblasts. Cancer Res. Nov. 1, 2000;60(21):6001-7.

Richardson JA et al. 2005, Characterization of osteogenic oxysterols and their molecular mechanism(s) of action, J Bone Miner Res 20:S1;S414.

Richardson JA, Amantea CM, Kianmahd B, Tetradis S, Lieberman JR, Hahn TJ, Parhami F. Oxysterol-induced osteoblastic differentiation of pluripotent mesenchymal cells is mediated through a PKC- and PKA-dependent pathway. J Cell Biochem. Apr. 1, 2007;100(5):1131-45 (same as 2006 in press).

Rickard DJ, Sullivan TA, Shenker BJ, Leboy PS, Kazhdan I. Induction of rapid osteoblast differentiation in rat bone marrow stromal cell cultures by dexamethasone and BMP-2. Dev Biol. Jan. 1994;161(1):218-28.

Riggs BL, Melton LJ 3rd. The prevention and treatment of osteoporosis. N. Engl J Med. Aug. 27, 1992;327(9):620-7. Review.

Riobó NA, Lu K, Ai X, Haines GM, Emerson CP Jr. Phosphoinositide 3-kinase and Akt are essential for Sonic Hedgehog signaling. Proc Natl Acad Sci U S A. Mar. 21, 2006;103(12):4505-10.

Rodan GA, Martin TJ. Therapeutic approaches to bone diseases. Science 2000; 289:1508-1514.

Rodda SJ, McMahon AP. Distinct roles for Hedgehog and canonical Wnt signaling in specification, differentiation and maintenance of osteoblast progenitors. Development. Aug. 2006;133(16):3231-44.

Ruan B, Wilson WK, Shroepfer GJ. An improved synthesis of (20R,22R)-cholest-5-ene-3β,20,22-triol, and intermediate in steroid hormone formation and an activator of nuclear orphan receptor LXRα. Steroids 1999; 64:385-395.

Rubin CD. Treatment considerations in the management of age-related osteoporosis. The American J Medical Sciences 1999; 318 (3):158-170.

Russell DW. Oxysterol biosynthetic enzymes. Biochimica et Biophysica Acta 2000; 1529:126-135.

Sanchez P, Hernández AM, Stecca B, Kahler AJ, DeGueme AM, Barrett A, Beyna M, Datta MW, Datta S, Ruiz i Altaba A. Inhibition of prostate cancer proliferation by interference with Sonic Hedgehog-GLI1 signaling. Proc Natl Acad Sci U S A. Aug. 24, 2004;101(34):12561-6.

Schaafsma et al. 2001. Delay of natural bone loss by higher intake of specific minerals and vitamins. Crit Rev Food Sci Nutr 41:225-249.

Schambony A, Wedlich D. Wnt-5A/Ror2 regulate expression of XPAPC through an alternative noncanonical signaling pathway. Dev Cell. May 2007;12(5):779-92.

Schroepfer GJ Jr. Oxysterols: modulators of cholesterol metabolism and other processes. Physiol Rev. Jan. 2000;80(1):361-554. Review.

Seo JB, Moon HM, Kim WS, Lee YS, Jeong HW, Yoo EJ, Ham J, Kang H, Park MG, Steffensen KR, Stulnig TM, Gustafsson JA, Park SD, Kim JB. Activated liver X receptors stimulate adipocyte differentiation through induction of peroxisome proliferator-activated receptor gamma expression. Mol Cell Biol. Apr. 2004;24(8):3430-44.

Shea CM, Edgar CM, Einhorn TA, Gerstenfeld LC. BMP treatment of C3H10T1/2 mesenchymal stem cells induces both chondrogenesis and osteogenesis. J Cell Biochem. Dec. 15, 2003;90(6):1112-27.

Shimaoka H, Dohi Y, Ohgushi H, Ikeuchi M, Okamoto M, Kudo A, Kirita T, Yonemasu K. Recombinant growth/differentiation factor-5 (GDF-5) stimulates osteogenic differentiation of marrow mesenchymal stem cells in porous hydroxyapatite ceramic. J Biomed Mater Res A. Jan. 1, 2004;68(1):168-76.

Shouhed D, Kha HT, Richardson JA, Amantea CM, Hahn TJ, Parhami F. Osteogenic oxysterols inhibit the adverse effects of oxidative stress on osteogenic differentiation of marrow stromal cells. J Cell Biochem 95:1276-1283; 2005.

Silva-Vargas V, Lo Celso C, Giangreco A, Ofstad T, Prowse DM, Braun KM, Watt FM. Beta-catenin and Hedgehog signal strength can specify number and location of hair follicles in adult epidermis without recruitment of bulge stem cells. Dev Cell. Jul. 2005;9(1):121-31.

Sohal RS, Mockett RJ, Orr WC. Mechanisms of aging: an appraisal of the oxidative stress hypothesis. Free Radic Biol Med. Sep. 1, 2002;33(5):575-86. Review.

Spinella-Jaegle S, Rawadi G, Kawai S, Gallea S, Faucheu C, Mollat P, Courtois B, Bergaud B, Ramez V, Blanchet AM, Adelmant G, Baron R, Roman-Roman S. Sonic hedgehog increases the commitment of pluripotent mesenchymal cells into the osteoblastic lineage and abolishes adipocytic differentiation. J Cell Sci 114:2085-2094; 2001.

Spiro RC, Thompson AY, Poser JW. Spinal fusion with recombinant human growth and differentiation factor-5 combined with a mineralized collagen matrix. Anat Rec. Aug. 1, 2001;263(4):388-95.

Stein GS, Lian JB. Molecular mechanisms mediating proliferation/differentiation interrelationships during progressive development of the osteoblast phenotype. Endocrine Rev 14:424-442; 1993.

Stewart GA, Hoyne GF, Ahmad SA, Jarman E, Wallace WA, Harrison DJ, Haslett C, Lamb JR, Howie SE. Expression of the developmental Sonic hedgehog (Shh) signalling pathway is up-regulated in chronic lung fibrosis and the Shh receptor patched1 is present in circulating T lymphocytes. J Pathol 199:488-495; 2003.

St-Jacques B, Hammerschmidt M, McMahon P. Indian hedgehog signaling regulates proliferation and differentiation of chondrocytes and is essential for bone formation. Genes Dev 1999; 13:2072-2086.

Suh JM, Gao X, McKay J, McKay R, Salo Z, Graff JM. Hedgehog signaling plays a conserved role in inhibiting fat formation. Cell Metab. Jan. 2006;3(1):25-34.

Swarthout JT, D'Alonzo RC, Selvamurugan N, Partridge NC. Parathyroid hormone-dependent signaling pathways regulating genes in bone cells. Gene. Jan. 9, 2002;282(1-2):1-17. Review.

Taipale J, Beachy PA. The Hedgehog and Wnt signalling pathways in cancer. Nature. May 17, 2001;411(6835):349-54. Review.

Taylor FR, Kandutsch AA, Gayen AK, Nelson JA, Nelson SS, Phirwa S, Spencer TA. 24,25-Epoxysterol metabolism in cultured mammalian cells and repression of 3-hydroxy-3-methylglutaryl-CoA reductase. J Biol Chem. Nov. 15, 1986;261(32):15039-44.

Väänänen HK. Mesenchymal stem cells. Ann Med. 2005;37(7):469-79. Review.

Valentin-Opran A, Wozney J, Csimma C, Lilly L, Riedel GE. Clinical evaluation of recombinant human bone morphogenetic protein-2. Clin Orthop & Related Res 2002; 305:110-120.

Velgova H, Cerny V, Sorm F, Slama K. Collect. Czech. Chem. Commun. 1969, 34: 3354-3375.

Vine DF, Mamo JCL, Beilin LJ, Mori TA, Croft KD. Dietary oxysterols are incorporated in plasma triglyceride-rich lipoproteins, incrase their susceptibility to oxidation and increase aortic cholesterol concentrations in rabbits. J Lipid Res 1998; 1995-2004.

Wang GJ, Cui Q, Balian G. The Nicolas Andry award. The pathogenesis and prevention of steroid-induced osteonecrosis. Clin Orthop Relat Res. Jan. 2000;(370):295-310.

Watson KE, Bostrom K, Ravindranath R, Lam T, Norton B, Demer LL. TGF-beta and 25-hydroxycholesterol stimulate osteoblast-like vascular cells to calcify. J Clin Invest 93:2106-2113; 1994.

Westendorf JJ, Kahler RA, Schroeder TM. nt signaling in osteoblasts and bone diseases. ene. Oct. 27, 2004;341:19-39. Review.

Woo BH, Fink BF, Page R, Schrier JA, Jo YW, Jiang G, DeLuca M, Vasconez HC, DeLuca PP. Enhancement of bone growth by sustained delivery of recombinant human bone morphogenetic protein-2 in a polymeric matrix. Pharm Res 2001; 18:1747-1753.

Yamaguchi A, Komori T, Suda T. Regulation of osteoblast differentiation mediated by bone morphogenetic proteins, hedgehogs, and Cbfa1. Endocrine Rev 2000; 21:393-411.

Yang D, Guo J, Divieti P, Bringhurst FR. Parathyroid hormone activates PKC-delta and regulates osteoblastic differentiation via a PLC-independent pathway. Bone. Apr. 2006;38(4):485-96. Epub Dec. 1, 2005.

Yang X, Karsenty G. Transcription factors in bone: developmental and pathological aspects. Trends Mol Med. Jul. 2002;8(7):340-5. Review.

Yoon ST, Boden SD. Osteoinductive molecules in orthopaedics: basic science and preclinical studies. Clin Orthop & Related Res 2002; 495:33-43.

Yoshida CA, Furuichi T, Fujita T, Fukuyama R, Kanatani N, Kobayashi S, Satake M, Takada K, Komori T. Core-binding factor beta interacts with Runx2 and is required for skeletal development. Nat Genet. Dec. 2002;32(4):633-8.

Yoshida K, Oida H, Kobayashi T, Maruyama T, Tanaka M, Katayama T, Yamaguchi K, Segi E, Tsuboyama T, Matsushita M, Ito K, Ito Y, Sugimoto Y, Ushikubi F, Ohuchida S, Kondo K, Nakamura T, Narumiya S. Stimulation of bone formation and prevention of bone loss by prostaglandin E EP4 receptor activation. Proc Natl Acad Sci U S A. Apr. 2, 2002;99(7):4580-5. Epub Mar. 26, 2002 (author typo: Yoshia).

Zanchetta P, Lagar de N, Guezennec J. Systematic effects on bone healing of a new hyaluronic acid-like bacterial exopolysaccharide. Calcif Tissue Int 2003; 73:232-236.

Zelcer N, Tontonz P. Liver X receptors as integrators of metabolic and inflammatory signaling. J Clin Invest 116:607-614; 2006.

Zhao M, Qiao M, Harris SE, Chen D, Oyajobi BO, Mundy GR. The zinc finger transcription factor Gli2 mediates bone morphogenetic protein 2 expression in osteoblasts in response to hedgehog signaling. Mol Cell Biol 26:6197-6208; 2006.

Zhao M, Qiao M, Oyajobi BO, Mundy GR, Chen D. E3 ubiquitin ligase Smurf1 mediates core-binding factor alpha1/Runx2 degradation and plays a specific role in osteoblast differentiation. J Biol Chem. Jul. 25, 2003;278(30):27939-44.

Ziros PG, Gil AP, Georgakopoulos T, Habeos I, Kletsas D, Basdra EK, Papavassiliou AG. The bone-specific transcriptional regulator Cbfa1 is a target of mechanical signals in osteoblastic cells. J Biol Chem. Jun. 28, 2002;277(26):23934-41.

Aghaloo et al.; Oxysterols enhance osteoblast differentiation in vitro and bone healing in vivo; J. Bone & Mineral Research 2005, 20(9): S361, Abstract M203, 27th Annual Meeting of American Society for Bone and Mineral Research.

Choo et al., Otolaryngology Head Neck Surgery 1999, 120: 84-91.

European Search Report in 241907 EP mailed Jun. 15, 2009 (EP 03749213.9).

European Search Report in 256918 EP mailed Jul. 1, 2009 (suppl., EP 06824888.9).

ISR for PCT/US06/012902 mailed Jul. 7, 2008.

ISR for PCT/US06/34374 mailed Jun. 16, 2008.

ISR for PCT/US07/016309 mailed Sep. 16, 2008.

ISR for PCT/US07/25833 mailed Sep. 11, 2008.

ISR for PCT/US08/013319 mailed Apr. 8, 2009.

Izumo N et al.; Lipophilic statins can be osteogenic by promoting osteoblastic calcification in a Cbfa1—and BMP-2-independent manner. Methods and Findings in Experimental and Clinical Pharmacology 2001, 23(7): 389-394.

Kadiyala et al.; Culture expanded canine mesenchymal stem cells possess osteochondrogenic potential in vivo and in vitro; Cell Transplantation 1997, 6(2): 125-134.

Lefevre A, Morera A-M, Saez JM. Adrenal cholesterol-binding protein: properties and partial purification. FEBS Letters 1978, 89(2): 287-292.

Mezey et al., Oral Diseases 2009, Abstract.

Mundy et al.; Science 1999, 286: 1946-1949.

Nakamura et al.; Stimulation of bone formation by intraosseous application of recombinant basic fibroblast growth factor in normal and ovariectomized rabbits; J. Orthopaedic Research 1997, 15(2): 307-313.

Office Action for U.S. Appl. No. 10/569,994 dated Jan. 2, 2009.

Office Action for U.S. Appl. No. 10/569,994 dated May 30, 2008.

Office Action for U.S. Appl. No. 10/569,994 dated Aug. 31, 2009.

Song et al., Chinese Journal of Reparative and Reconstructive Surgery 2002, 16: 384-387.

Written Opinion for PCT/US04/028162 mailed Feb. 22, 2005.

Written Opinion for PCT/US06/012902 mailed Jul. 7, 2008.

Written Opinion for PCT/US06/34374 mailed Jun. 16, 2008.

Written Opinion for PCT/US07/016309 mailed Sep. 16, 2008.

Written Opinion for PCT/US07/05073 mailed Oct. 29, 2007.

Written Opinion for PCT/US08/013319 mailed Apr. 8, 2009.

Yeh et al., Journal of Cell Biochemistry 2002, 87: 292-304.

Zhang et al.; Cyclooxygenase-2 regulates mesenchymal cell differentiation into the osteoblast lineage and is critically involved in bone repair; J. Clinical Investigation 2002, 109(11): 1405-1415.

Albrektsson T., Johansson C. Osteoinduction, osteoconduction and osseointegration. 2001. Eur Spine J. 10:S96-S101.

Dimmeler et al. HMG-CoA reductase inhibitors (statins) increase endothelial progenitor cells via the PI 3-kinase/Akt pathway. 2001. Journal of Clin Invest. 108:(3): 391-397.

Rao et al. Lovastatin-mediated G1 arrest is through inhibition of the proteosome, independent of hydroxymethyl glutarl-CoA reductase. 1997. Proc. Natl. Acad. Sci. 96: 7797-7802.

Steitz et al. Smooth Muscle Cell Phenotypic Transition Associated With Calcification: Upregulation of Cbfa1 and Downregulation of Smooth Muscle Lineage Markers. 2001. Circ. Res. 89:1147-1154.

Tintut et al. Multilineage Potential of Cells From the Artery Wall. 2003. Circulation.108: 2505-2510.

Wada et al. Calcification of Vascular Smooth Muscle Cell Cultures : Inhibition by Osteopontin. 1999. Circ. Res. 8:166-178.

Wada et al. Lack of Positive Correlation Between Statin Ue and Bone Mineral Density in Japanese Subjects With Type 2 Diabetes. 2000. Arch Intern Med. 160:2865.

Wang et al. Lipid Clearing Agents in Steroid-Induces Osteoporosis. 1995. J Formos Med Assoc. 94(10): 589-592.

* cited by examiner

| Treatment | TAr (mm2) | BAr (mm2) | BAr % TAr |
|---|---|---|---|
| Vehicle (n=6) | 2135.4 ± 415.8 | 892.7 ± 279.9 | 41.0 ± 6.1 |
| 22R+20S (n=6) | 1730.9 ± 409.5 | 850.3 ± 202.6 | 49.3* ± 4.2 |

0.2 mm

AGENTS AND METHODS FOR ENHANCING BONE FORMATION

GOVERNMENT SPONSORSHIP

This research is sponsored by U.S. National Institutes of Health/National Institutes of Aging, Grant No. P60 AG 10415-11, awarded by the National Institute of Health/National Institutes of Aging. The U.S. Government has certain rights in this invention.

BACKGROUND OF THE INVENTION

Normal bone remodeling, which occurs throughout the adult life in order to preserve the integrity of the skeleton, involves bone resorption by osteoclasts and bone formation by osteoblasts. Thus, any interference between the balance in bone formation and bone resorption can affect bone homeostasis, bone formation and repair.

The osteoblasts come from a pool of marrow stromal cells (also known as mesenchymal stem cells; MSC). These cells are present in a variety of tissues and are prevalent in bone marrow stroma. MSC are pluripotent and can differentiate into osteoblasts, chondrocytes, fibroblasts, myocytes, and adipocytes.

Osteoporosis is a major cause of morbidity and mortality in the elderly and the annual cost to the U.S. health care system is at least ten billion dollars. Both men and women suffer from osteoporotic bone loss with age. Decreases in sex hormones with age are thought to impact these detrimental changes. For example, osteoporosis increases in women after menopause.

Accumulating evidence suggests that the number and activity of osteoblastic cells decrease with age, however the reason for this change is not clear. Additionally, there is an increase in formation of adipocytes in osteoporotic bone marrow that appears to be at the expense of osteoblast formation. Moreover, the volume of adipose tissue in bone increases with age in normal subjects, and is substantially elevated in age-related osteoporosis, with the number of adipocytes adjacent to bone trabeculae increasing in parallel to the degree of trabecular bone loss. Based on this and similar observations, it has been suggested that bone loss in age-related osteoporosis is at least in part due to a shift from osteoblastic differentiation to the adipocytic pathway.

Bone fracture healing is impaired in the elderly, and others demonstrating a reduced number and activity of the MSC that would normally migrate into the fracture site and allow for new bone formation to occur.

At present, the only treatments for osteoporosis are those that target bone resorption by osteoclasts. These FDA approved therapeutics include the bisphosphonates, hormone replacement therapies, such as selective estrogen receptor modulators, calcitonin, and vitamin D/calcium supplementation. However, these treatments only result in only small improvements in bone mass, and are not sufficient for total prevention or treatment of osteoporosis.

Currently, the only FDA approved anabolic agent for the treatment of osteoporosis is parathyroid hormone (PTH). PTH is currently thought to increase bone formation by inhibiting osteoblast apoptosis. PTH has been found to increase bone mass upon intermittent injection and reduce bone fracture incidence in osteoporotic patients. However, the dose must be strictly regulated since continuous treatment with PTH and/or its accumulation may have adverse systemic effects upon the patient. Additionally, PTH treatment is quite expensive. Consequently, PTH treatment has been reserved for only the most severely osteoporotic patients.

Other potential therapeutics for enhancing bone formation by osteoblasts include sodium fluoride and growth factors that have a positive effect on bone (for example insulin-like growth factors I and II and transforming growth factor beta). However, thus far these factors have had undesirable side effects.

The use of stem cells for treating bone related disorders in humans has also been examined. For example, osteogenesis imperfecta is a skeletal disease in which the patient's osteoblasts do not make collagen I in a proper form, resulting in the brittle bones. Infusion of osteoblastic progenitor stem cells from a healthy individual into a diseased individual has been shown to improve bone density in these patients. Further, stem cells can be isolated from an individual, expanded in vitro, stimulated to become cartilage forming chondrocytes, and infused back into arthritic joints where the cartilage is remade.

Therefore, agents and methods for regulating bone homeostasis, bone formation and bone repair are desired.

SUMMARY OF THE INVENTION

The present invention is related to agents and methods for maintaining bone homeostasis, enhancing bone formation and/or enhancing bone repair.

More specifically, the invention may include the systemic and/or local application agents for maintaining bone homeostasis, enhancing bone formation and/or enhancing bone repair.

More specifically, the invention may include the use of agents which stimulate osteoblastic bone formation. The invention may include the use of agents which influence the differentiation of MSC into osteobalsts. Agents which may be useful in this invention to effect osteoblastic differentiation include, but are not limited to individual oxysterols, such as 22(R)-, 22(S)-, 20(S), and 25-hydroxycholesterol, pregnanolone individually or in combination with each other. Particular examples of combinations of oxysterols which may be useful in the invention are 22R- and 20S-hydroxycholesterol, as well as 22S- and 20S-hydroxycholesterol. The invention may further include any portion of the oxysterol molecule which is found to be active in effecting osteoblastic differentiation or bone formation. The invention may further include the activation of a molecule at which the oxysterols are active in effecting osteoblastic differentiation or bone formation. The invention may also include other lipid molecules or analogs designed to mimic the active portions of the above oxysterols, which would act similarly to the parent molecules, via similar mechanisms of action, and similar receptors that would have a positive impact on bone homeostasis.

The invention may include the use of agents which inhibit osteoclastic bone resorption. Agents which may be useful in this invention to effect osteoclastic bone resorption include, but are not limited to, bisphosphonates, the selective estrogen receptor modulators, calcitonin, and vitamin D/calcium supplementation. The invention may also include the use of agents which induce osteoblastic bone formation. Agents which may be useful in this invention include, but are not limited to PTH, sodium fluoride and growth factors, such as insulin-like growth factors I and II and transforming growth factor beta.

The invention may include a method of systemic delivery or localized treatment with agents for maintaining bone homeostasis, enhancing bone formation and/or enhancing bone repair. The invention may include a method of systemic delivery or localized treatment with differentiated osteoblastic cells for maintaining bone homeostasis, enhancing bone formation and/or enhancing bone repair.

In one application of the invention, the method may be applied to induce the local repair of bone, such as in periodontitis, periodontal regeneration, alveolar ridge augmentation for tooth implant reconstruction, treatment of non-union fractures. In one application of the invention, the method may be applied to treat bone related disorders, such as osteoporosis.

The invention may also include implants having coatings of substances or seeded with differentiated cells for inducing bone formation or enhancing bone repair. The invention may also include the application of substances or differentiated cells at a site where bone formation or bone repair is desired. For example, implants may include, but are not limited to pins, screws and plates that are used to immobilize a fracture, enhance bone formation, or stabilize a prosthetic implant by stimulating bone formation or bone repair.

DETAILED DESCRIPTION

Figure 1:
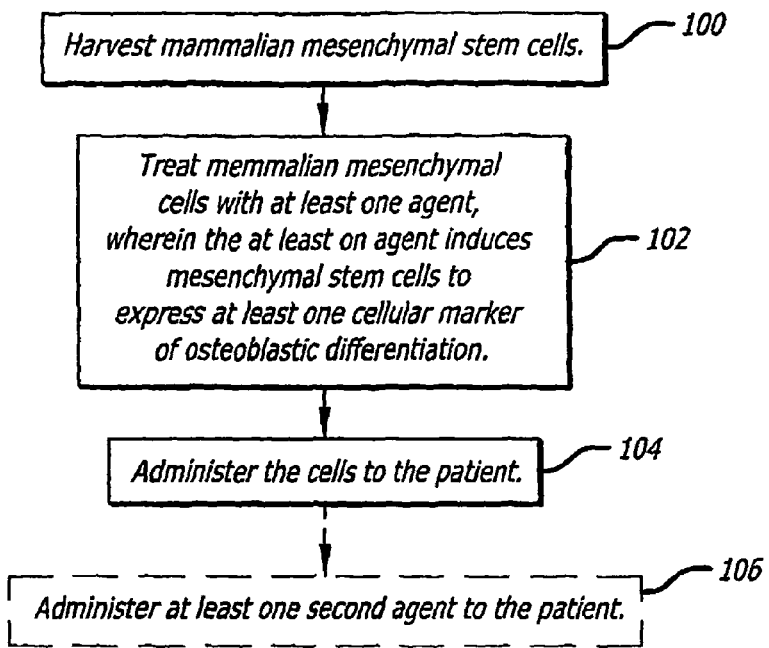
FIG. 1 depicts a flowchart of one method according to this invention.

The present invention is related to agents and methods for maintaining bone homeostasis, enhancing bone formation and/or enhancing bone repair.

More specifically, the invention may include the systemic and/or local application of agents for maintaining bone homeostasis, enhancing bone formation and/or enhancing bone repair. Clinical indices of a method or compounds ability to maintain bone homeostasis is evidenced by improvements in bone density at different sites through out the body as assessed by DEXA scanning. Enhanced bone formation in a healing fracture is routinely assessed by regular X-ray of the fracture site at selected time intervals. More advanced techniques for determining the above indices such as quantitative CT scanning may be used.

More specifically, the invention may include the use of agents which stimulate osteoblastic bone formation. The invention may include the use of agents which influence the differentiation of MSC into osteobalsts.

Agents which may be useful in this invention to affect osteoblastic differentiation include, but are not limited to individual or combinations of oxysterols.

Oxysterols. The ability of oxysterols to induce of osteogenic differentiation and mineralization and inhibit adipogenic differentiation may provide a benefit to maintaining bone homeostasis, inducing bone formation or inducing bone repair.

Oxysterols form a large family of oxygenated derivatives of cholesterol that are present in the circulation and in tissues. Oxysterols are endogenous, oxygenated derivatives of cholesterol and are important in regulating cholesterol biosynthesis. Oxysterols are formed by autooxidation, as a secondary byproduct of lipid peroxidation, or by the action of specific monooxygenases, most of which are members of the cytochrome P450 enzyme family. Oxysterols may be derived from dietary intake. Oxysterols have been implicated in regulation of other physiologic and/or pathologic processes including cholesterol metabolism, steroid production, apoptosis, atherosclerosis, necrosis, inflammation, and immunosuppression.

Cholesterol biosynthesis has recently been shown to be involved in marrow stromal cells (MSC) differentiation, as demonstrated by the inhibitory effects of HMG-CoA reductase inhibitors, which could be reversed by mevalonate. Further, oxysterols have been demonstrated to have osteogenic potential as evidenced by their ability to induce osteoblastic differentiation, and additionally mineralization of MSC in vitro. Finally, oxysterols have been demonstrated to have anti-adipogenic effects and inhibit adipocyte differentiation of MSC.

The in vitro models used to show the osteogenic and anti-adipogenic effects of oxysterols are valid and have been used previously in demonstrating similar behaviors of other compounds including bone morphogenetic proteins (BMP). Osteoprogenitor cells including marrow stromal cells (M2 cells) used in this report, have been shown to act similarly to those present in vivo in animals and humans. These in vitro models have also previously been able to successfully predict the in vivo osteogenic effects of compounds such as BMP and insulin like growth factors (IGF). In addition, it has been demonstrated the osteogenic effects of the oxysterols in a bone organ culture model using mouse neonatal calvaria. This organ culture model has also previously been used to successfully predict osteogenic effect of different compounds including BMP in vivo. Therefore it is anticipated that based on these similar findings, oxysterols will have osteogenic effects in vivo in animals and humans. Demonstration of osteogenic effects of a compound in these in vitro and organ culture models are necessary prior to trials that would demonstrate their effects in vivo in animals and humans.

Agents which may be useful in this invention to effect osteoblastic differentiation include, but are not limited to individual oxysterols, such as 22(R)-, 22(S)-, 20(S), and 25-hydroxycholesterol, pregnanolone individually or in combination with each other. Particular examples of combinations of oxysterols which may be useful in the invention are 22R- and 20S-hydroxycholesterol, as well as 22S- and 20S-hydroxycholesterol. The invention may further include any portion of the oxysterol molecule which is found to be active in affecting osteoblastic differentiation or bone formation. The invention may further include the activation of a molecule at which the oxysterols are active in effecting osteoblastic differentiation or bone formation. The invention may also include other lipid molecules or analogs designed to mimic the active portions of the above oxysterols, which would act similarly to the parent molecules, via similar mechanisms of action, and similar receptors that would have a positive impact on bone homeostasis.

Mechanism of action. The mechanisms by which oxysterols are physiologically active have been examined, and oxysterols have been shown to be active and effected by a variety of cellular pathways. First, the effects of oxysterols on osteoblastic differentiation have been demonstrated to be potentiated by a cytochrome P450 inhibitor. The effects of oxysterols on osteoblastic differentiation are also mediated by enzymes in the arachidonic acid metabolic pathway, i.e. cyclooxygenase (COX) and phospholipase A2, and ERK. Second, arachidonic acid, released for example from cellular phospholipase activity positively effects the oxysterol effect on osteoblastic differentiation. Third, prostaglandins, including prostaglandin E2 and osteogenic prostanoids, metabolized by the COX enzymes positively effects the oxysterol effect on osteoblastic differentiation. Fourth, extra-cellular signal-regulated kinase (ERK) activity is increased by oxysterols and is correlated with osteoblastic differentiation and mineralization. Therefore, these agents or agents which stimulate the mechanism of oxysterol action may also be useful in this invention.

Further, oxysterols are known to bind to and activate nuclear hormone receptors called liver X receptors (LXR) which then bind to consensus binding sites on the promoters of genes that are regulated by LXR. Additional orphan nuclear hormone receptors may also serve as for oxysterol binding sites that could mediate some of the regulatory effects of oxysterols. The invention may include the use of agents which inhibit osteoclastic bone resorption.

The invention may include a method of systemic delivery or localized treatment with agents for maintaining bone homeostasis, enhancing bone formation and/or enhancing bone repair.

The invention includes a medicament for use in the treatment of bone disorders comprising a therapeutically effective dosage of at least one oxysterol selected from the group comprising 20S-hydroxycholesterol, 22S-hydroxycholesterol, 22R-hydroxycholesterol, 25-hydroxycholesterol, or pregnanolone, or an active portion of any one of 20S-hydroxycholesterol, 22S-hydroxycholesterol, 22R-hydroxycholesterol, 25-hydroxycholesterol, or pregnanolone.

Therapeutically effective dose. A therapeutically effective dose of a agent useful in this invention is one which has a positive clinical effect on a patient as measured by the ability of the agent to improve bone homeostasis, bone formation or bone repair, as described above. The therapeutically effective dose of each agent can be modulated to achieve the desired clinical effect, while minimizing negative side effects. The dosage of the agent may be selected for an individual patient depending upon the route of administration, severity of the disease, age and weight of the patient, other medications the patient is taking and other factors normally considered by an attending physician, when determining an individual regimen and dose level appropriate for a particular patient.

By way of example, the invention may include elevating endogenous, circulating oxysterol levels over the patient's basal level. In a normal adult levels are about 10-400 nm/ml depending on age and type of oxysterol, as measured by mass spectrometry. Those skilled in the art of pharmacology could determine the dosage and route effective to raise the circulating oxysterol levels from the patient's basal level.

Dosage Form. The therapeutically effective dose of an agent included in the dosage form may be selected by considering the type of agent selected and the route of administration. The dosage form may include a agent in combination with other inert ingredients, including adjutants and pharmaceutically acceptable carriers for the facilitation of dosage to the patient, as is known to those skilled in the pharmaceutical arts. In one embodiment, the dosage form may be an oral preparation (e.g., liquid, capsule, caplet or the like) which when consumed results in the elevated levels of the agent in the body. The oral preparation may comprise carriers including diluents, binders, time release agents, lubricants and disinigrants.

The dosage form may be provided in a topical preparation (e.g., lotion, creme, ointment, transdermal patch, or the like) for dermal application. The dosage form may also be provided in preparations for subcutaneous (such as in a slow-release capsule), intravenous, intraparitoneal, intramuscular or respiratory application, for example.

Any one or a combination of agents may be included in a dosage form. Alternatively, a combination of agents may be administered to a patient in separate dosage forms. A combination of agents may be administered concurrent in time such that the patient is exposed to at least two agents for treatment.

Additional Agents. The invention may include treatment with an additional agent which acts independently or synergistically with at least a first agent to maintaining bone homeostasis, enhancing bone formation and/or enhancing bone repair.

Additional agents may be agents which stimulate the mechanistic pathway by which oxysterols enhance osteoblastic differentiation. Therefore, classes of agents which may be useful in this invention alone or in combination with oxysterols include, but are not limited to cytochrome P450 inhibitors, such as SKF525A. Other classes of agents useful in the invention include phospholipase activators, or arachadonic acid. Other classes of agents useful in the invention include COX enzyme activators, or prostaglandins or osteogenic prostanoids. Other classes of agents useful in the invention include ERK activators.

The invention may include combination treatments with oxysterols and other therapeutics which affect bone formation, repair or homeostasis. For example, oxysterols in combination with bisphosphonates, hormone therapy treatemtns, such as estrogen receptor modulators, calcitonin, and vitamin D/calcium supplementation, PTH (such as Forteo or teriparatide, Eli Lilly, sodium fluoride and growth factors that have a positive effect on bone, such as insulin-like growth factors I and II and transforming growth factor beta. Those skilled in the art would be able to determine the accepted dosages for each of the therapies using standard therapeutic dosage parameters.

The invention may include a method of systemic delivery or localized treatment with differentiated osteoblastic cells for maintaining bone homeostasis, enhancing bone formation and/or enhancing bone repair. This treatment may be administered alone or in combination with administration of other agent(s) to the patient, as described above. FIG. 1 depicts a flowchart of one method according to this invention. In this embodiment of the method, mammalian mesenchymal stem cells may be harvested, form the patient or a cell donor (100). The cells may then be treated with at least one agent to induce osteoblastic differentiation of the cells (102). The cells may then be re-administered to the patient, either systemically or at a selected site at which bone homeostasis, bone formation or bone repair is desired (104). Additionally, the patent may by treated locally or systemically with at least one second agent which effects bone homeostasis, bone formation or bone repair (106).

In this aspect of the invention, MSC may be treated with an agent(s) to stimulate osteoblastic differentiation, as measured by any one of the increase in alkaline phosphatase activity, calcium incorporation, mineralization or osteocalcin mRNA expression, or other indicators of osteoblastic differentiation. In one embodiment of the invention MSC cells are harvested from a patient, treated with at least one oxysterol, and osteoblastic cells are administered to the patient.

The invention may include administering osteoblastically differentiated MSC systemically to the patient.

The invention may include placing osteoblastically differentiated MSC at selected locations in the body of a patient. In one embodiment of the invention, cells may be injected at a location at which bone homeostasis, formation and/or repair is desired.

In one application of the invention, the agents and methods may be applied to, but are not limited to the treatment or to slow the progression of bone related disorders, such as osteoporosis.

In applications of the invention, the agents and methods may be applied to, but are not limited to application of cells or agents to a surgical or fracture site, in periodontitis, periodontal regeneration, alveolar ridge augmentation for tooth implant reconstruction, treatment of non-union fractures, sites of knee/hip/joint repair or replacement surgery.

Figure 2A:
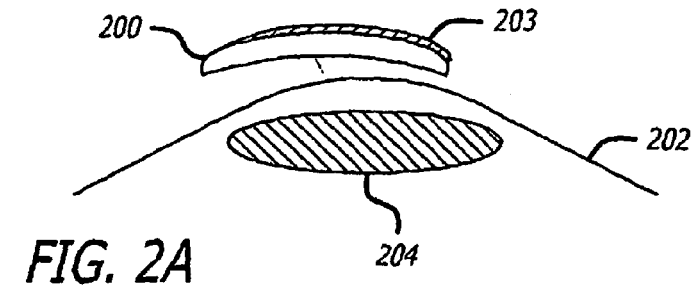
FIG. 2 depicts two embodiments of the present invention.

FIG. 2 depicts two embodiments of the present invention. In FIG. 2A, the invention may include implants (200) for use in the human body comprising, a substrate having a surface (201), wherein at least the surface of the implant includes at least one oxysterol (203) in an amount sufficient to induce bone formation in the surrounding bone tissue, or implant includes mammalian cells capable of osteoblastic differentiation, or osteoblastic mammalian cells, or a combination thereof for inducing bone formation or enhancing bone repair. The implant may also For example, implants may include, but are not limited to pins, screws, plates or prosthetic joints which may be placed in the proximity of or in contact with a bone (202) that are used to immobilize a fracture, enhance bone formation, or stabilize a prosthetic implant by stimulating formation or repair of a site of bone removal, fracture or other bone injury (204).

Figure 2B:
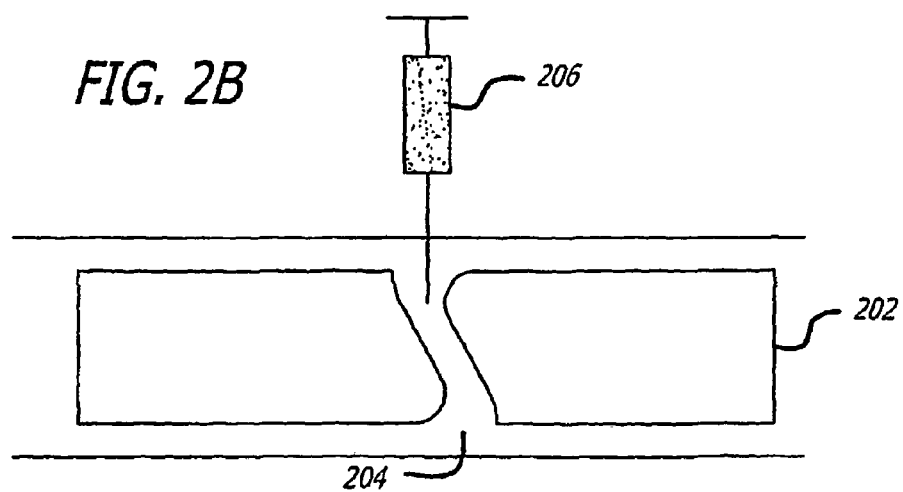

As shown in FIG. 2B, the invention may also include the application of at least one agent or differentiated cells (206) in the proximity of or in contact with a bone (202) at a site of bone removal, fracture or other bone injury (204) where bone formation or bone repair is desired.

EXAMPLES

Materials: Oxysterols, beta-glycerophosphate (βGP), silver nitrate, oil red O were obtained from Sigma (St. Louis, Mo., U.S.A.), RPMI 1640, alpha modified essential medium (α-MEM), and Dulbecco's modified Eagle's medium (DMEM) from Irvine Scientific (Santa Ana, Calif., U.S.A.), and fetal bovine serum (FBS) from Hyclone (Logan, Utah, U.S.A.). PD98059 was purchased from BIOMOL Research Labs (Plymouth Meeting, Pa., U.S.A.), TO-901317, SC-560, NS-398, Ibuprofen, and Flurbiprofen from Cayman Chemical (Ann Arbor, Mich., U.S.A.), AGA and AACOCF3 from Calbiochem (La Jolla, Calif., U.S.A.), recombinant human BMP2 from R&D Systems (Minneapolis, Minn., U.S.A.). Antibodies to phosphorylated and native ERKs were obtained from New England Biolabs (Beverly, Mass., U.S.A.) and troglitazone from Sankyo (Tokyo, Japan).

Cells: M2-10B4 mouse marrow stromal cell line obtained from American Type Culture Collection (ATCC, Rockville, Md., U.S.A.) was derived from bone marrow stromal cells of a (C57BL/6J×C3H/HeJ) F1 mouse, and support human and murine myelopoiesis in long-term cultures (as per ATCC) and have the ability to differentiate into osteoblastic and adipocytic cells. Unless specified, these cells were cultured in RPMI 1640 containing 10% heat-inactivated FBS, and supplemented with 1 mM sodium pyruvate, 100 U/ml penicillin, and 100 U/ml streptomycin (all from Irvine Scientific).

MC3T3-E1 mouse preosteoblastic cell line was purchased from ATCC and cultured in α-MEM containing 10% heat-inactivated FBS and supplements as described above.

C3H-10T1/2 mouse pluripotent embryonic fibroblast cells were a kindly provided by Dr. Kristina Bostrom (UCLA) and were cultured in DMEM containing 10% heat-inactivated FBS and supplements as described above. Primary mouse marrow stromal cells were isolated from male 4-6 months old C57BL/6J mice, and cultured and propagated as previously reported. Parhami, F. et al., *J. Bone Miner. Res.* 14, 2067-2078 (1999), herein incorporated by reference in its entirety.

Alkaline phosphatase activity assay: Colorimetric alkaline phosphatase (ALP) activity assay on whole cell extracts was performed as previously described.

Von Kossa and oil red O staining—Matrix mineralization in cell monolayers was detected by silver nitrate staining as previously described. Oil red O staining for detection of adipocytes was performed as previously described.

$^{45}$Ca incorporation assay—Matrix mineralization in cell monolayers was quantified using the $^{45}$Ca incorporation assay as previously described.

Western blot analysis—After treatments, cells were lysed in lysis buffer, protein concentrations determined using the Bio-Rad protein assay (Hercules, Calif. U.S.A.), and SDS- PAGE performed as previously described. Probing for native and phosphorylated ERKs was performed as previously reported.

RNA isolation and Northern blot analysis—Following treatment of cells under appropriate experimental conditions, total RNA was isolated using the RNA isolation kit from Stratagene (La Jolla, Calif., U.S.A.). Total RNA (10 mg) was run on a 1% agarose/formaldehyde gel and transferred to Duralon-UV membranes (Strategene, Calif., U.S.A.) and cross-linked with UV light. The membranes were hybridized overnight at 60 degree C. with $^{32}$P-labeled mouse osteocalcin cDNA probe, mouse lipoprotein lipase (LPL), mouse adipocyte protein 2 (aP2) PCR-generated probes, human 28S or 18S rRNA probes obtained from Geneka Biotechnology (Montreal, Quebec, Canada) and Maxim Biotech (San Francisco, Calif., U.S.A.), respectively. The PCR products were generated using primer sets synthesized by Invitrogen (Carlsbad, Calif., U.S.A.) with the following specifications: mouse aP2 gene (accession no. M13261); sense (75-95) 5'-CCAGG-GAGAACCAAAGTTGA-3' (SEQ. ID. NO. 1), antisense (362-383) 5'-CAGCACTCACCCACTTCTTTC-3' (SEQ. ID. NO. 2), generating a PCR product of 309 base pairs. Mouse LPL (accession no. XM_134193); sense (1038-1058) 5'-GAATGAAGAAAACCCCAGCA-3' (SEQ. ID. NO. 3), antisense (1816-1836) 5'-TGGGCCATTAGATTCCTCAC-3' (SEQ. ID. NO. 4), generating a PCR product of 799 base pairs. The PCR products were gel-purified and sequenced by the UCLA sequencing core, showing the highest similarity to their respective GenBank entries. Following hybridization, the blots were washed twice at room temperature with 2×SSC+0.1% SDS, and then twice at 60 degree C. with 0.5× SSC+0.1% SDS, and exposed to X-ray film. The extent of gene induction was determined by densitometry.

Statistical Analyses—Computer-assisted statistical analyses were performed using the StatView 4.5 program. All p values were calculated using ANOVA and Fisher's projected least significant difference (PLSD) significance test. A value of $p<0.05$ was considered significant.

Example A

Osteogenic Effects of Oxysterols in MSC

Figure 3A:
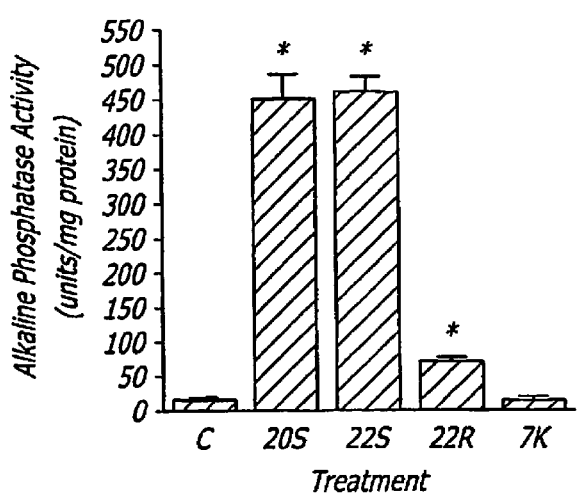
FIG. 3: A) is a bar graph depicting the effect of various oxysterols on alkaline phosphatase activity in M2 cells; B) is a bar graph depicting the effect of a combination of oxysterols at various doses on alkaline phosphatase activity in M2 cells; C) is a depiction of von Kossa staining of M2 cells exposed to various conditions; D) is a bar graph depicting the effect of a combination of oxysterols at various doses on calcium incorporation in M2 cells; E) is a radiogram of Northern blotting for osteocalcin mRNA in M2 cells exposed to a control or combination of oxysterols for 4 or 8 days; F) is a bar graph depicting the relative densometric units of osteocalcin mRNA in M2 cells exposed to a control or combination of oxysterols for 4 or 8 days.

Test 1: M2 cells at confluence were treated with control vehicle (C), or 10 μM oxysterols, in an osteogenic medium consisting of RPMI 1640 to which 10% fetal bovine serum (FBS), 50 μg/ml ascorbate and 3 mM beta-glycerophosphate (βGP) were added. After 3 days of incubation, alkaline phosphatase (ALP) activity was determined in cell homogenates by a colorimetric assay. Results from a representative of five experiments are shown, reported as the mean±SD of quadruplicate determinations, normalized to protein concentration (*$p<0.01$ for C vs. oxysterol-treated cells). FIG. 3A is a bar graph depicting the effect of various oxysterols on alkaline phosphatase activity in M2 cells.

Figure 3B:
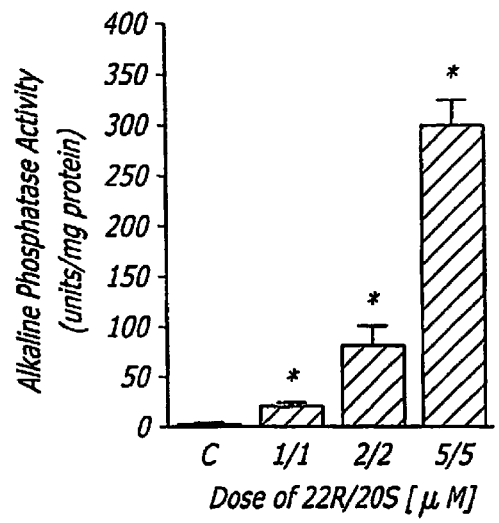

M2 cells at confluence were treated in osteogenic medium with control vehicle (C) or a combination of 22R and 20S oxysterols, at the indicated concentrations. ALP activity was measured after 3 days as described above. Results from a representative of four experiments are shown, reported as the mean±SD of quadruplicate determinations, normalized to protein concentration (*$p<0.01$ for C vs. oxysterols). FIG. 3B is a bar graph depicting the effect of a combination of oxysterols at various doses on alkaline phosphatase activity in M2 cells.

Figure 3D:
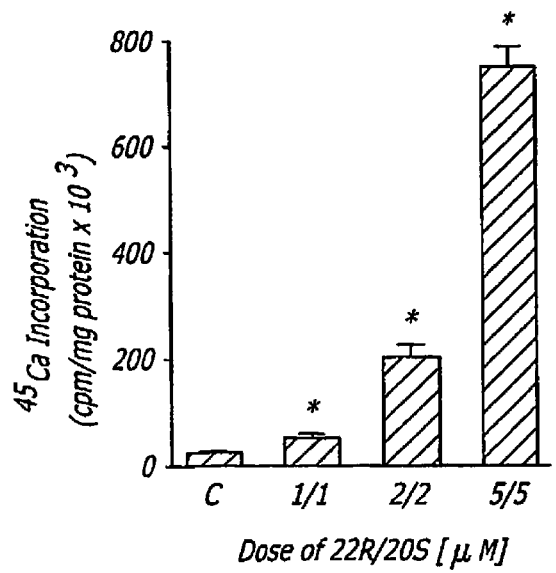
Figure 3F:
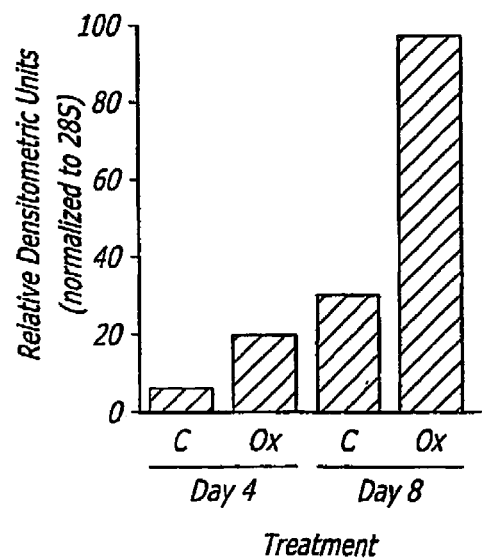
Figure 3C:
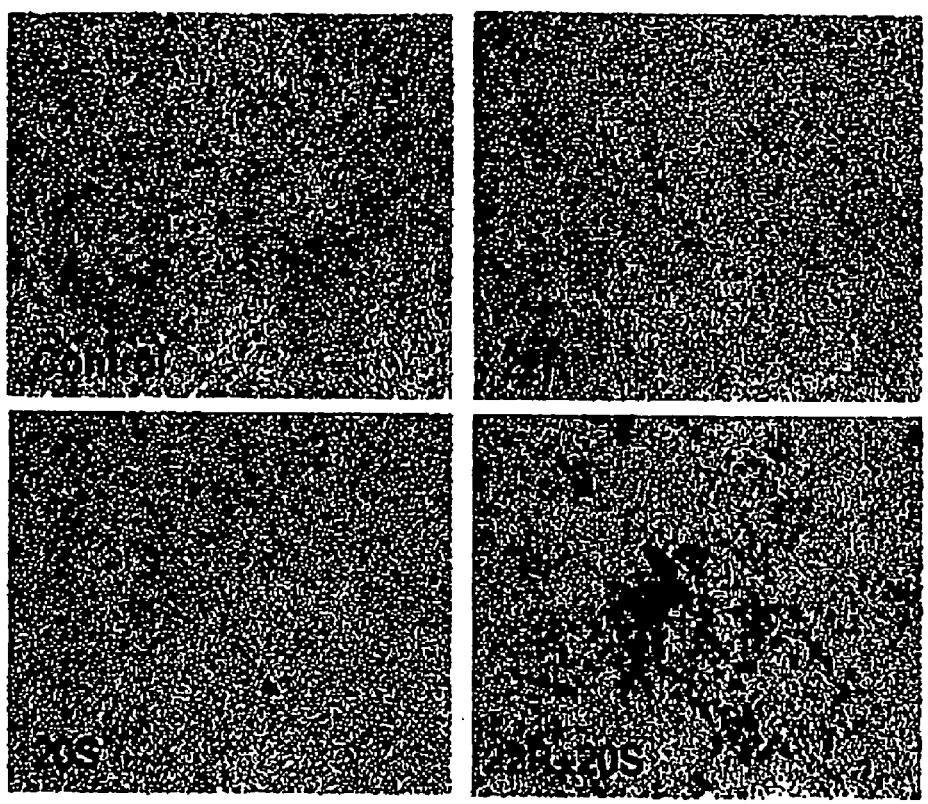

M2 cells at confluence were treated in osteogenic medium with control vehicle or 5 μM oxysterols, alone or in combination as indicated. After 14 days, mineralization was identified by a von Kossa staining, which appears black. FIG. 3C is a depiction of von Kossa staining of M2 cells exposed to various conditions.

M2 cells were treated with control vehicle (C) or a combination of 22R and 20S oxysterols at increasing concentrations. After 14 days, matrix mineralization in cultures was quantified using a $^{45}$Ca incorporation assay. Results from a representative of four experiments are shown, reported as the mean±SD of quadruplicate determinations, normalized to protein concentration (*$p<0.01$ for C vs. oxysterol-treated cultures). FIG. 3D is a bar graph depicting the effect of a combination of oxysterols at various doses on calcium incorporation in M2 cells.

Figure 3E:
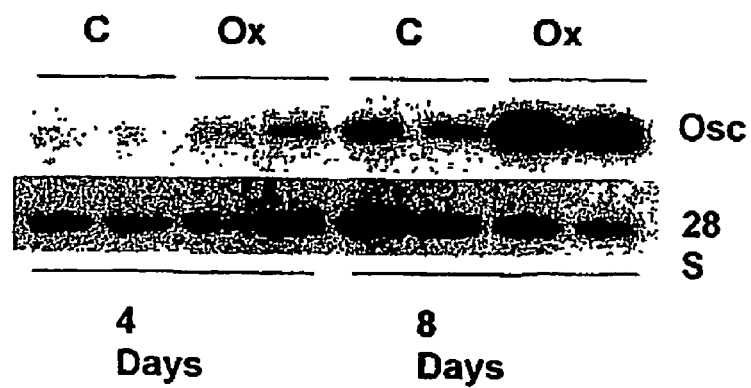

M2 cells at confluence were treated with control vehicle (C) or a combination of 22R and 20S oxysterols (5 μM each) in osteogenic medium. After 4 and 8 days, total RNA from duplicate samples was isolated and analyzed for osteocalcin (Osc) and 28S rRNA expression by Northern blotting as described. FIG. 3E is a radiogram of Northern blotting for osteocalcin mRNA in M2 cells exposed to a control or combination of oxysterols for 4 or 8 days. FIG. 3F is a bar graph depicting the relative demsometric units of osteocalcin mRNA in M2 cells exposed to a control or combination of oxysterols for 4 or 8 days. Data from densitometric analysis of the Northern blot is shown in (F) as the average of duplicate samples, normalized to 28S rRNA.

Results Test 1: In cultures of MSC, stimulation of alkaline phosphatase activity, osteocalcin gene expression and mineralization of cell colonies are indices of increased differentiation into osteoblast phenotype. Specific oxysterols, namely 22(R)-hydroxycholesterol (22R), 20(S)-hydroxycholesterol (20S), and 22(S)-hydroxycholesterol (22S), induced alkaline phosphatase activity, an early marker of osteogenic differentiation, in pluripotent M2-10B4 murine MSC (M2). 7-ketocholesterol (7K) did not induce alkaline phosphatase activity in these cells.

The induction of alkaline phosphatase activity was both dose- and time-dependent at concentrations between 0.5-10 μM, and showed a relative potency of 20S>22S>22R. A 4-hour exposure to these oxysterols followed by replacement with osteogenic medium without oxysterols was sufficient to induce alkaline phosphatase activity in M2 cells, measured after 4 days in culture.

Individual oxysterols (22R, 20S and 22S) at concentrations between 0.5-10 μM were unable to induce mineralization or osteocalcin gene expression after as many as 14 days of treatment (data not shown). However, alkaline phosphatase activity (FIG. 3B), robust mineralization (FIGS. 3C and D) and osteocalcin gene expression (FIGS. 3E and F) were all induced in M2 cultures by a combination of the 22R+20S or 22S+20S oxysterols.

Test 2: M2 cells were grown in RPMI medium containing 10% fetal bovine serum (FBS). At confluence, the cells were treated in RPMI containing 5% FBS plus ascorbate at 50 μg/ml and β-glycerophosphate at 3 mM to induce osteoblastic differentiation. Adipogenic differentiation was induced by treating the cells in growth medium plus 10 ~M troglitazone. A vehicle (C) or oxysterol treatment was applied to cells in a variety of doses (in μM): 20S-Hydroxycholesterol, 25-Hydroxycholesterol, 22R-Hydroxycholesterol; 22S-Hydroxycholesterol; 7-ketocholesterol. Cells were always treated at 90% confluence. After 4 days, alkaline phosphatase activity was determined in whole cell lysates and normalized to protein. Alternatively, MSC cultures were prepared and treated with oxysterols as described above. Cells were treated at 90% confluence with the combination of 22R-Hydroxycholesterol and 20S-Hydroxycholesterol, each at 5 uM, for 4 to 96 hours. The oxysterols where removed and fresh media without oxysterols was added for a total duration of 96 hours. Alkaline phosphatase activity was measured in whole cell extracts and normalized to protein.

Figure 4A:
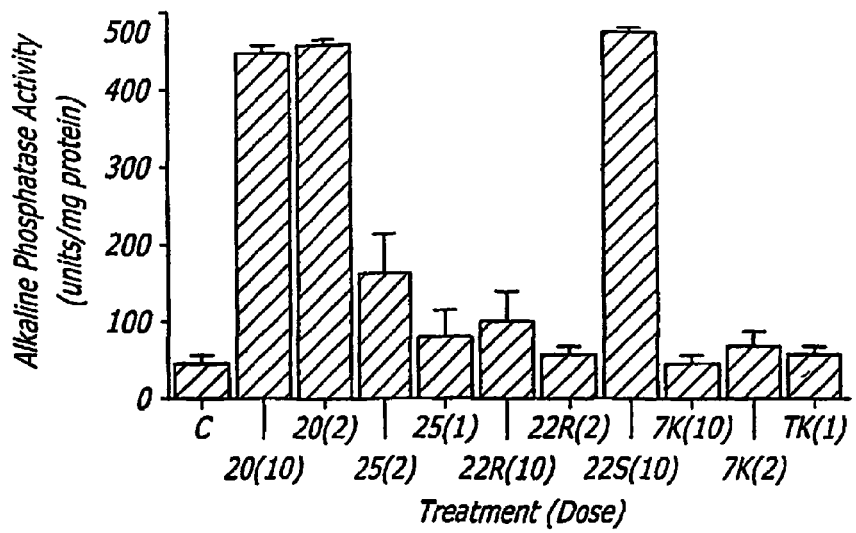
FIG. 4: A) is a bar graph depicting the effect of various oxysterols at various doses on M2 cells; B) is a bar graph depicting the effect of various oxysterols at various doses on M2 cells; C) is a bar graph depicting the effect of duration of treatment with oxysterols on M2 cells; D) is a bar graph depicting the effect of various dose combinations of oxysterols on M2 cells; E) is a bar graph depicting the effect of various dose combinations of oxysterols on M2 cells.

Results Test 2: FIG. 4A is a bar graph depicting the effect of various oxysterols at various doses on M2 cells after 4 days of exposure. Oxysterols induced alkaline phosphatase activity, an early marker of osteoblastic differentiation.

Figure 4B:
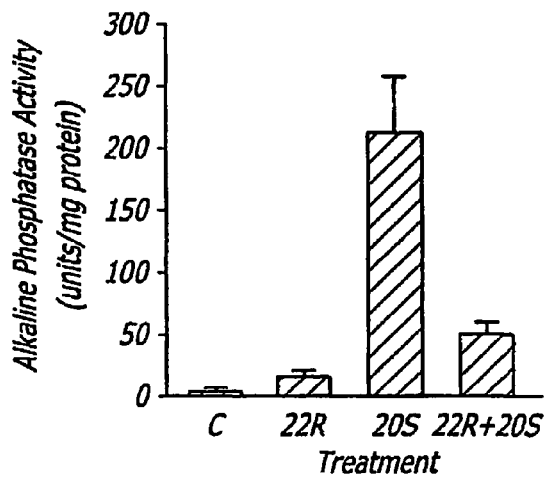

FIG. 4B is a bar graph depicting the effect of various oxysterols at various doses on M2 cells after 24 hours of treatment. Cells were treated at 90% confluence with vehicle (C), or oxysterols 22R-Hydroxycholeterol or 20S-Hydroxycholesterol, each at 5 µM, alone or in combination. After 24 hours, the cells were rinsed and media replaced with out oxysterols. After 4 days, alkaline phosphatase activity was measured in whole cell extracts and normalized to protein. Alkaline phosphatase activity was induced several fold after only 24 hours of treatment with the oxysterols.

Figure 4C:
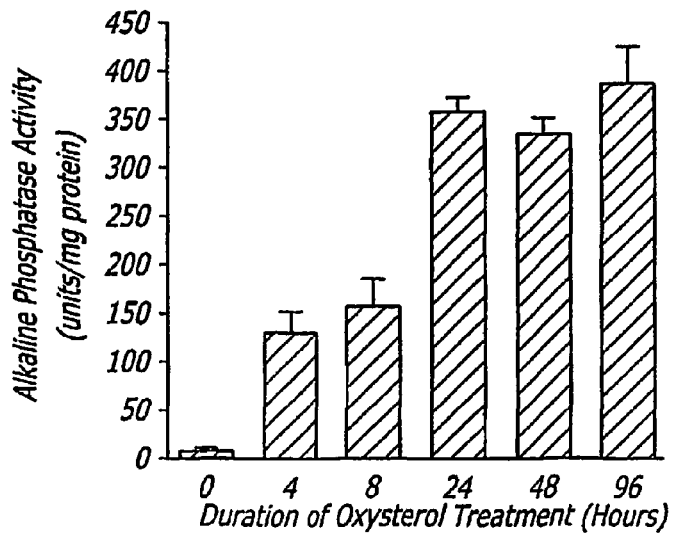

FIG. 4C is a bar graph depicting the effect of duration of treatment with oxysterols on M2 cells. Treatment with a combination oxysterols (22R-hydroxycholesterol and 20S-hydroxycholesterol, each at 5 µM induced alkaline phosphatase activity after 4-96 hours of treatment as measured 4 days post-treatment.

Figure 4D:
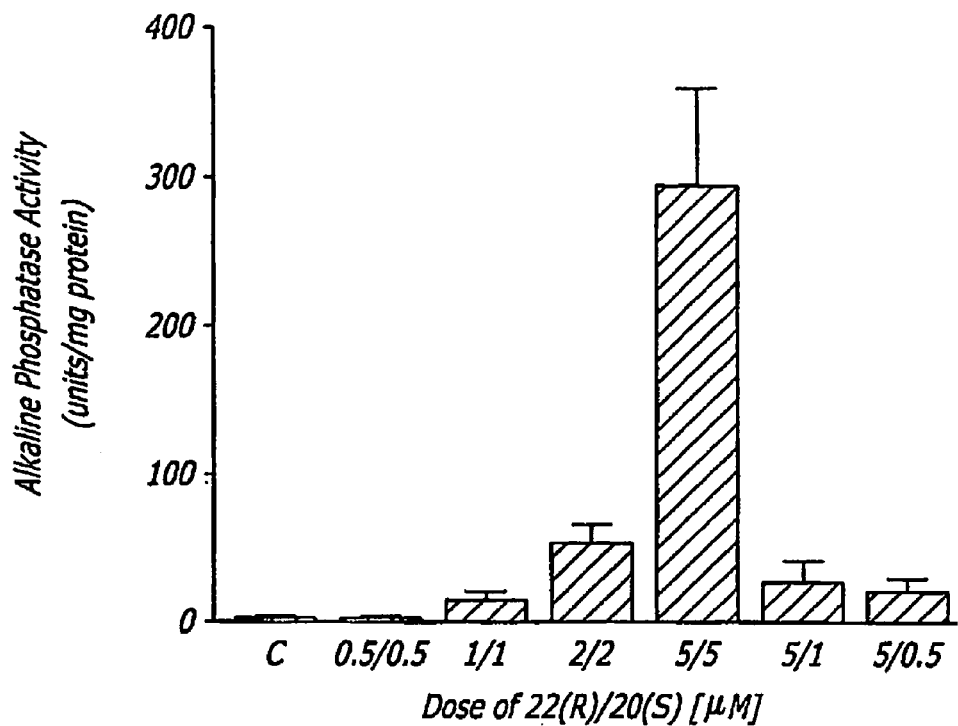

FIG. 4D is a bar graph depicting the effect of various dose combinations of oxysterols on M2 cells. The effect of the combination oxysterols on M2 cells was dose-dependent for the induction of alkaline phosphatase activity.

Figure 4E:
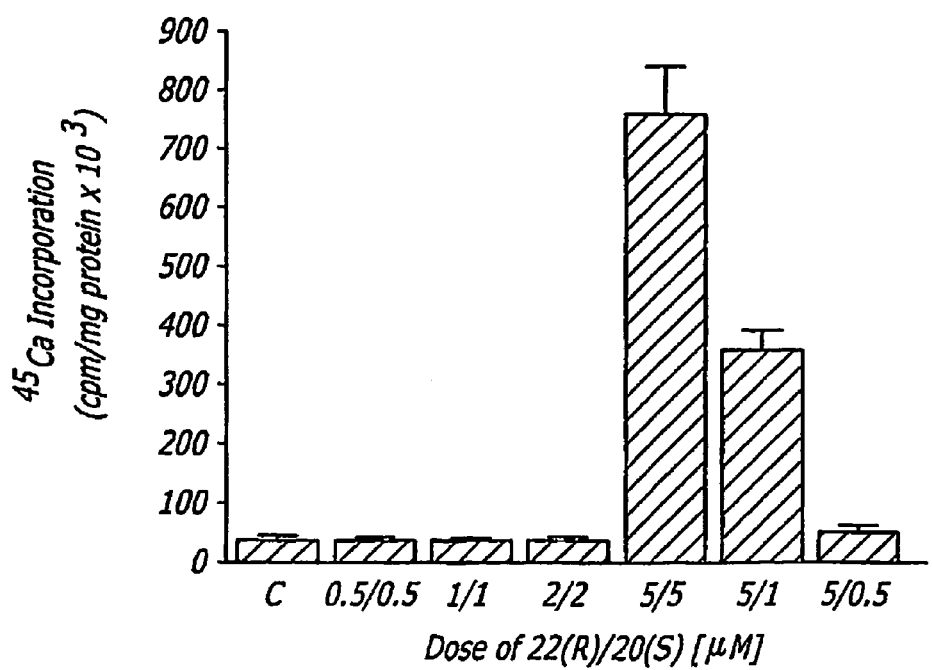

FIG. 4E is a bar graph depicting the effect of various dose combinations of oxysterols on M2 cells. Treatment with the combination doses of 22R- and 20S-Hydroxycholesterol. After 10 days, $^{45}$Ca incorporation was measured to assess bone mineral formation, and normalized to protein. The effect of combination oxysterols on M2 cells was dose-dependent for the induction of bone mineral formation as well.

Example B

Cytochrome P450 Inhibition of Oxysterol Effects

M2 cells were treated at 90% confluence with vehicle (C), or oxysterols 20S-Hydroxycholesterol or 22S-Hydroxycholesterol at (0.5 µM) or (1 µM), in the absence or presence of cytochrome P450 inhibitor (SKF525A 10 µM (+)). MSC cultures were also treated at 90% confluence with vehicle (C), or 20S-Hydroxycholesterol (2 µM), in the absence or presence of cytochrome P450 activator (Benzylimidazole 50 µM) or SKF525A (10 µM). After 4 days, alkaline phosphatase activity was measured in whole cell extracts and normalized to protein.

Figure 5A:
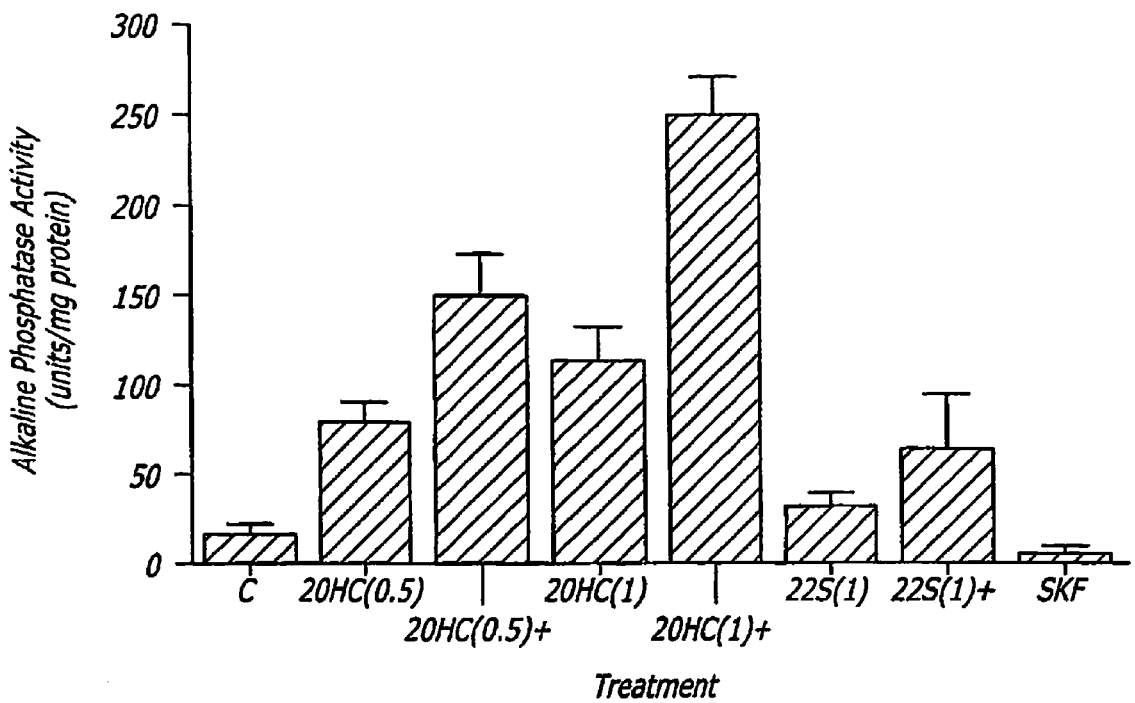
FIG. 5: A) is a bar graph depicting the effect of oxysterols and cytochrome P450 inhibitor SKF525A on M2 cells; B) is a bar graph depicting the effect of oxysterols and cytochrome P450 activator Benzylimidazole and inhibitor SKF525A M2 cells.

Results Example B: FIG. 5A is a bar graph depicting the effect of oxysterols and cytochrome P450 inhibitor SKF525A on marrow stromal cells. After 4 days, alkaline phosphatase activity was measured in whole cell extracts and normalized to protein. The use of the cytochrome P450 inhibitor potentiated the osteogenic effects of the oxysterols, suggesting that oxysterols are metabolized and inhibited by the cytochrome P450 enzymes.

Figure 5B:
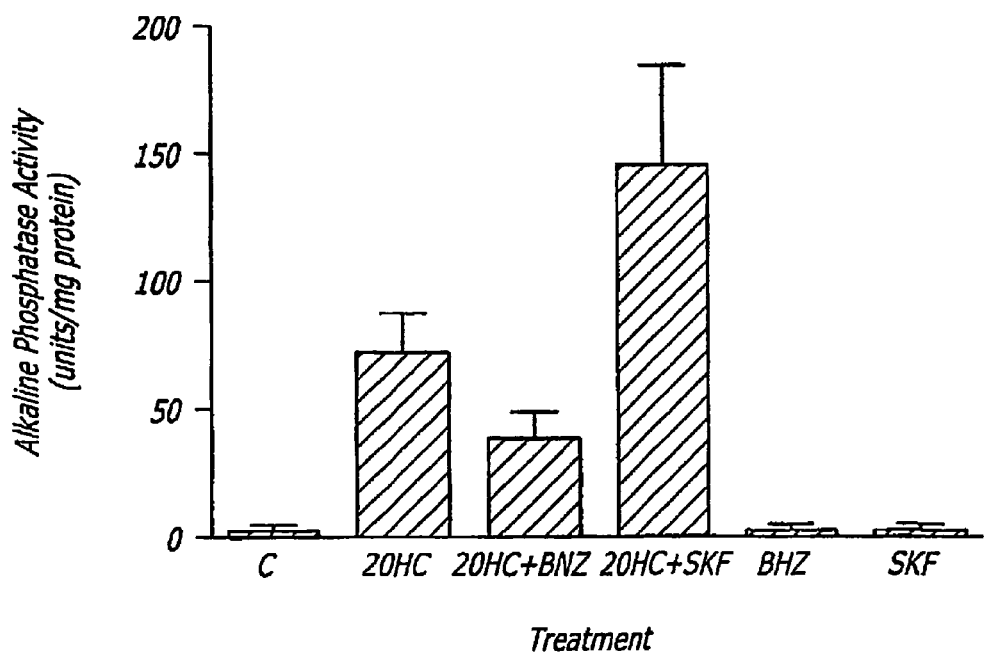

FIG. 5B is a bar graph depicting the effect of oxysterols and cytochrome P450 activator Benzylimidazole and inhibitor SKF525A on M2 cells. Treatment with stimulator of cytochrome P450 enzymes, Benzylimidazole, inhibited oxysterol effects, perhaps through enhancing oxysterol degradation.

Example D

Inhibition of Adipogenesis in MSC by Oxysterols

Adipogenesis of adipocyte progenitors including MSC is regulated by the transcription factor peroxisome proliferator activated receptor γ (PPARγ), that upon activation by ligand-binding, regulates transcription of adipocyte specific genes.

Figure 6:
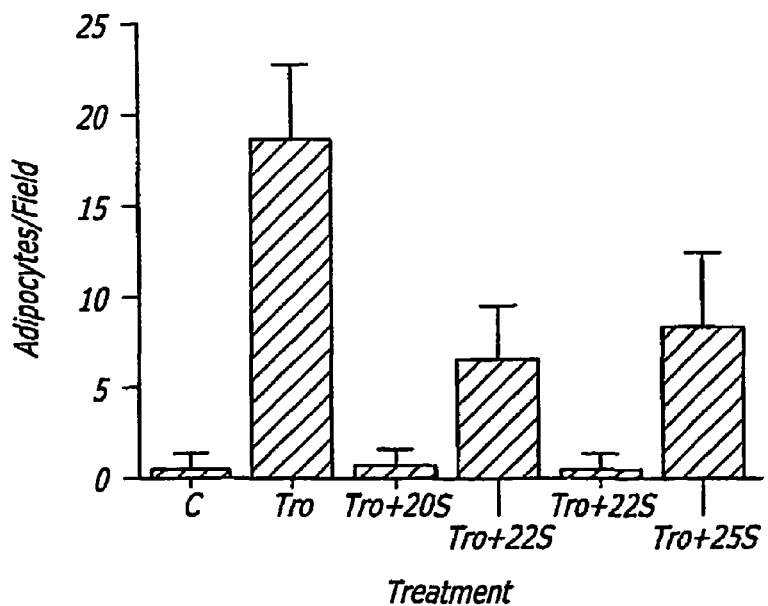
FIG. 6 is a bar graph depicting the effect of oxysterols on reducing adipogenesis of M2 cells.

Test 1: M2 cells at 90% confluence were treated with vehicle (C), PPAR-γ activator, troglitazone 10 uM (Tro), alone or in combination with 10 µM oxysterols 20S-, 22R-, or 25S-hydroxycholesterol. After 8 days, adipocytes were identified by oil Red 0 staining and quantified by counting under a phase contrast microscope. FIG. 6A is a bar graph depicting the effect of oxysterols on reducing adipogenesis of MSC. The osteogenic oxysterols inhibited adipogenesis in MSC cultures.

Test 2: (A) M2 cells at confluence were treated in RPMI containing 10% FBS with control vehicle or 10 µM troglitazone (Tro) in the absence or presence of 10 µM 20S or 22S oxysterols. After 10 days, adipocytes were visualized by oil Red O staining and quantified by light microscopy, shown in (B). Data from a representative of four experiments are shown, reported as the mean SD of quadruplicate determinations (p<0.001 for Tro vs. Tro+20S and Tro+22S). (C) M2 cells were treated at confluence with 10 µM Tro, alone or in combination with 10 µM 20S oxysterol. After 10 days, total RNA was isolated and analyzed for lipoprotein lipase (LPL), adipocyte P2 gene (aP2) or 18S rRNA expression by Northern blotting as described (Ref). Data from densitometric analysis of the Northern blot is shown in (D) as the average of duplicate samples, normalized to 18S rRNA.

FIG. 7: A) are depictions of M2 cell cultures in which adipocytes are visualized by oil Red O stain; B) is a bar graph depicting the number of adipocytes/field in each treatment group; C) is a radiogram of Northern blotting for lipoprotein lipase, adipocyte P2 gene or 18S rRNA in M2 cells exposed to a control or treatment; D) is a bar graph depicting the relative demsometric units of lipoprotein lipase, adipocyte P2 gene mRNA in M2 cells exposed to a control or treatment.

Figure 7A:
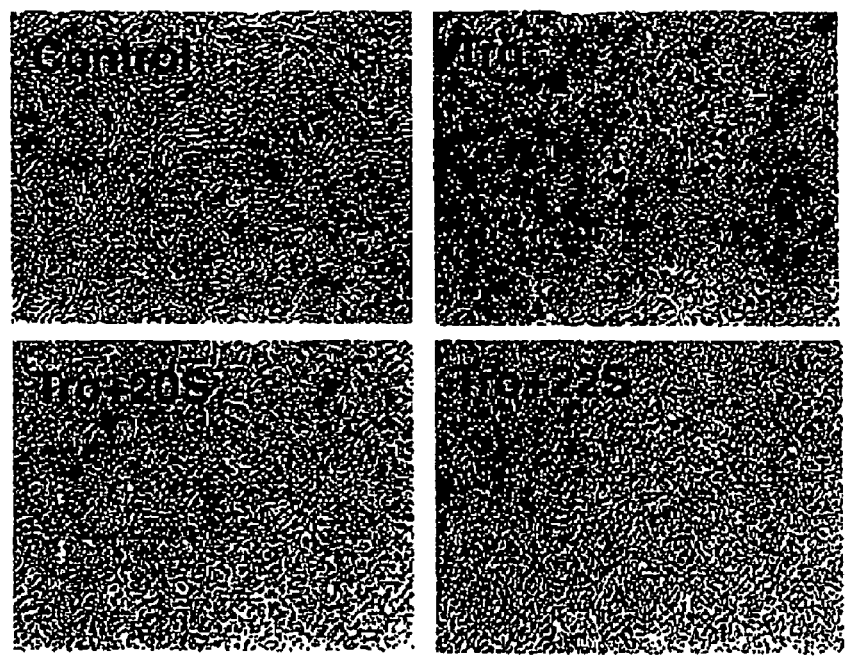
FIG. 7: A) are depictions of M2 cell cultures in which adipocytes are visualized by oil Red O stain; B) is a bar graph depicting the number of adipocytes/field in each treatment group; C) is a radiogram of Northern blotting for lipoprotein lipase, adipocyte P2 gene or 18S rRNA in M2 cells exposed to a control or treatment; D) is a bar graph depicting the relative demsometric units of lipoprotein lipase, adipocyte P2 gene mRNA in M2 cells exposed to a control or treatment.
Figure 7C:
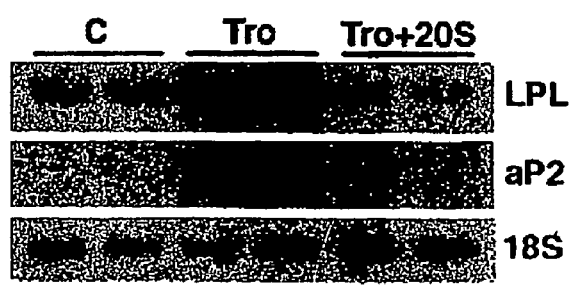

In M2 cells treated with Tro (PPARγ activator, Troglitazone (Tro)) to induce adipogenesis, 20S, 22S, and 22R, alone or in combination, inhibited adipogenesis. The relative anti-adipogenic potency of these oxysterols was similar to their relative potency in stimulating alkaline phosphatase activity in M2 cells, with 20S>22S>22R. Similar to its lack of osteogenic effect, 7K was also unable to inhibit adipogenesis in M2 cells (data not shown). Inhibition of adipogenesis was also assessed by an inhibition of the expression of the adipogenic genes lipoprotein lipase (LPL) and adipocyte P2 gene (aP2) by 20S (FIGS. 7C and D). Inhibitory effects of these oxysterols on adipogenesis were also demonstrated using C3H10T1/2 and primary mouse MSC, in which adipogenesis was induced either by Tro or a standard adipogenic cocktail consisting of dexamethasone and isobutylmethylxanthine.

Example E

Mechanism of Oxysterol Effects

Liver X receptors (LXR) are nuclear hormone receptors that in part mediate certain cellular responses to oxysterols. LXRα is expressed in a tissue specific manner, whereas LXRβ is ubiquitously expressed. By Northern blot analysis we demonstrated the expression of LXRβ, but not LXRα, in confluent cultures of M2 cells (data not shown). In order to assess the possible role of LXR in mediating the effects of osteogenic oxysterols, we examined whether activation of LXRβ by the pharmacologic LXR ligand TO-901317 (TO) had effects similar to those exerted by 22R and 20S in M2 cells.

Test 1: TO at 1-10 μM caused a dose-dependent inhibition of alkaline phosphatase activity in M2 cells (C: 18±2; ligands used at 10 μM: 22R=45±5; 20S=140±12; and TO=3±0.5 activity units/mg protein±SD; $p<0.01$ for C vs. all ligands). Furthermore, TO treatment did not induce osteocalcin gene expression or mineralization after 10 days. Therefore, the osteogenic effects of the oxysterols on M2 cells thus far appears to be independent of the LXR-beta receptor, as suggested by the potent osteogenic activity of the non-LXR oxysterol ligand 22S and the lack of osteogenic effects in response to the LXR ligand TO.

Figure 8:
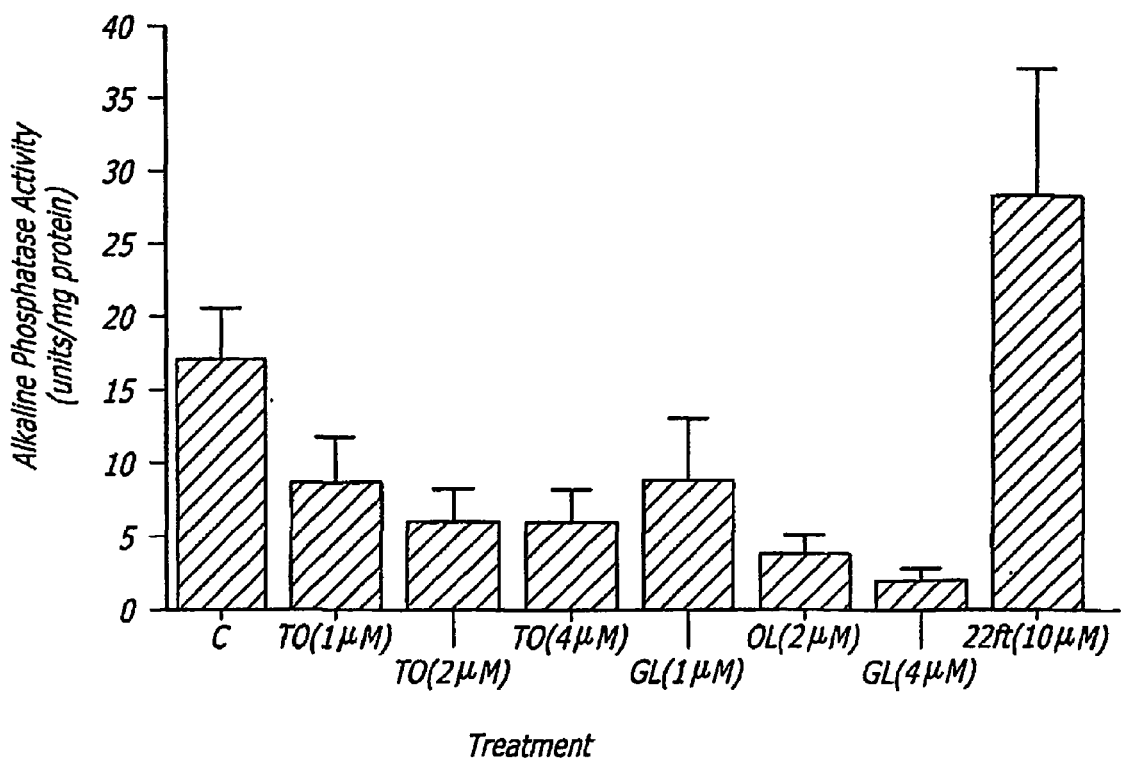
FIG. 8 is a bar graph depicting the effect of synthetic LXR activators on M2 cells.

Test 2: MSC cells at 90% confluence were treated with vehicle (C), or two unrelated LXR ligands (TO and GL at 1-4 μM), or 22R-hydroxycholesterol (10 μM). After 4 days, alkaline phosphatase activity was measured in whole cell lysates and normalized to protein. FIG. 8 is a bar graph depicting the effect of LXR activators on inhibiting osteoblastic differentiation of MSC. LXR-beta is present in MSC, however the osteogenic effects of the oxysterols described above appear not to be through LXR-beta since treatment with specific activators of LXR inhibited osteoblastic differentiation and mineralization of those cells.

Example F

Mechanism of Osteogenic Activity of Oxysterols in MSC

Mesenchymal cell differentiation into osteoblasts is regulated by cyclooxygenase (COX) activity. COX-1 and COX-2 are both present in osteoblastic cells, and appear to be primarily involved in bone homeostasis and repair, respectively. Metabolism of arachidonic acid into prostaglandins, including prostaglandin E2 (PGE2), by the COXs mediates the osteogenic effects of these enzymes. COX products and BMP2 have complementary and additive osteogenic effects.

(A) M2 cells at confluence were pretreated for 4 hours with control vehicle (C) or 10 μM COX-1 inhibitor SC-560 (SC) in osteogenic medium as described earlier. Next, a combination of 22R and 20S oxysterols (RS, 2.5 μM each) were added in the presence or absence of SC as indicated. After 3 days, ALP activity was measured as described earlier. Data from a representative of three experiments are shown, reported as the mean±SD of quadruplicate determinations, normalized to protein concentration ($p<0.001$ for RS vs. RS+SC). (B) M2 cells were treated as described in (A) and after 10 days matrix mineralization in cultures was quantified by a $^{45}$Ca incorporation assay as described earlier. Results from a representative of three experiments are shown, reported as the mean±SD of quadruplicate determinations, normalized to protein concentration. (C) M2 cells were pretreated with 20 μM SC for 4 hours, followed by the addition of RS in the presence or absence of SC as described above. After 8 days, total RNA was isolated and analyzed for osteocalcin (Osc) and 18S rRNA expression by Northern blotting as previously described. Data from densitometric analysis of the Northern blot is shown in (D) as the average of duplicate samples, normalized to 18S rRNA. (E) M2 cells at confluence were pretreated for 2 hours with control vehicle (C), or PLA$_2$ inhibitors ACA (25 μM) and AACOCF3 (AAC, 20 μM), in osteogenic medium. Next, a combination of 22R and 20S oxysterols (RS, 2.5 μM) was added in the presence or absence of the inhibitors as indicated. After 3 days, ALP activity was measured as previously described. Data from a representative of three experiments are shown, reported as the mean±SD of quadruplicate determinations, normalized to protein concentration ($p<0.01$ for RS vs. RS+ACA and RS+AAC). (F) M2 cells were treated as described in (E). After 10 days, matrix mineriliazation in cultures was quantified using a $^{45}$Ca incorporation assay as previously described. Results from a representative of three experiments are shown, reported as the mean of quadruplicate determinations±SD, normalized to protein concentration ($p<0.01$ for RS vs. RS+ACA and RS+AAC).

FIG. 9: A) is a bar graph depicting the effect of COX-1 inhibitor or oxysterol treatment on alkaline phosphatase activity in M2 cells; B) is a bar graph depicting the effect of COX-1 inhibitor or oxysterol treatment on calcium incorporation in M2 cells; C) is a radiogram of Northern blotting for osteoclastin or 18S rRNA in M2 cells exposed to COX-1 inhibitor or oxysterol treatment; D) is a bar graph depicting the relative demsometric units of osteoclastin mRNA in M2 cells exposed to COX-1 inhibitor or oxysterol treatment; E) is a bar graph depicting the effect of PLA$_2$ inhibitors or oxysterol treatment on alkaline phosphatase activity in M2 cells; and F) is a bar graph depicting the effect of PLA$_2$ inhibitors or oxysterol treatment on calcium incorporation in M2 cells.

Figure 9C:
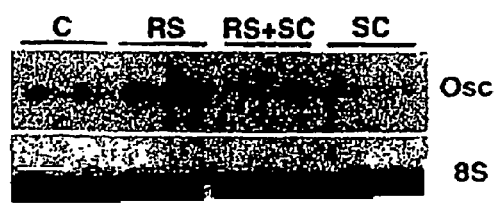
FIG. 9: A) is a bar graph depicting the effect of COX-1 inhibitor or oxysterol treatment on alkaline phosphatase activity in M2 cells; B) is a bar graph depicting the effect of COX-1 inhibitor or oxysterol treatment on calcium incorporation in M2 cells; C) is a radiogram of Northern blotting for osteoclastin or 18S rRNA in M2 cells exposed to COX-1 inhibitor or oxysterol treatment; D) is a bar graph depicting the relative demsometric units of osteoclastin mRNA in M2 cells exposed to COX-1 inhibitor or oxysterol treatment; E) is a bar graph depicting the effect of $PLA_2$ inhibitors or oxysterol treatment on alkaline phosphatase activity in M2 cells; and F) is a bar graph depicting the effect of $PLA_2$ inhibitors or oxysterol treatment on calcium incorporation in M2 cells.
Figure 7B:
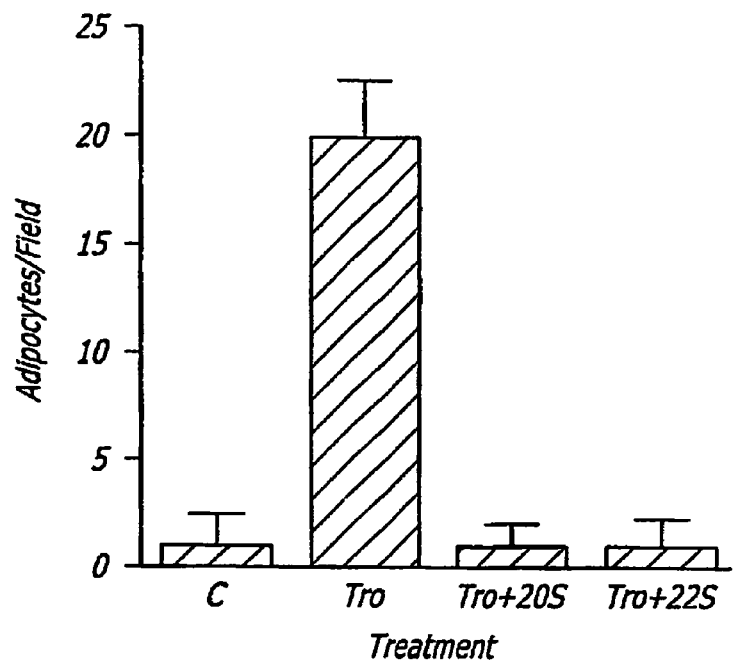
Figure 7D:
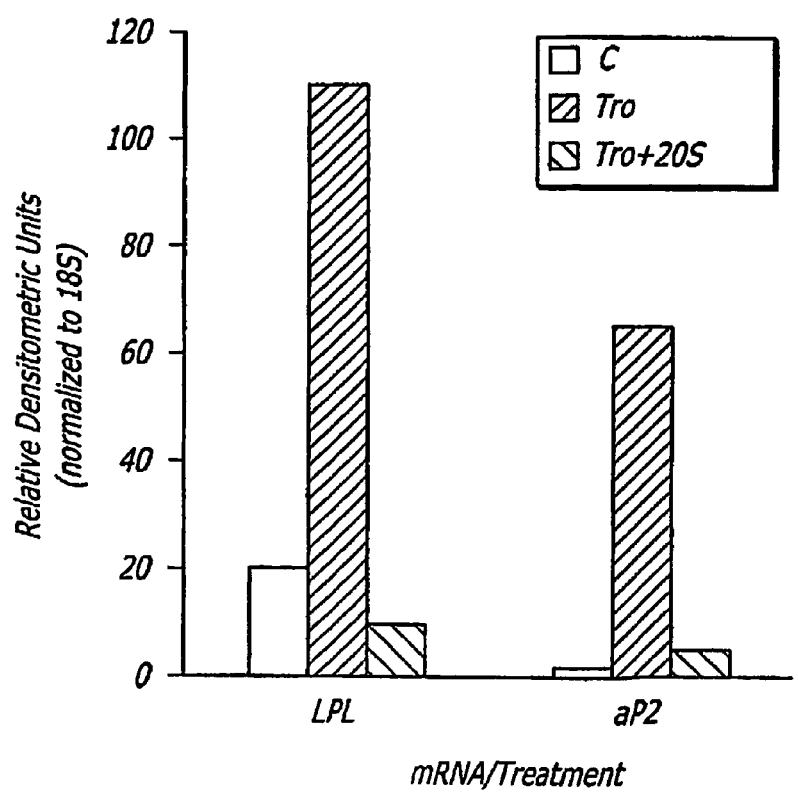
Figure 9A:
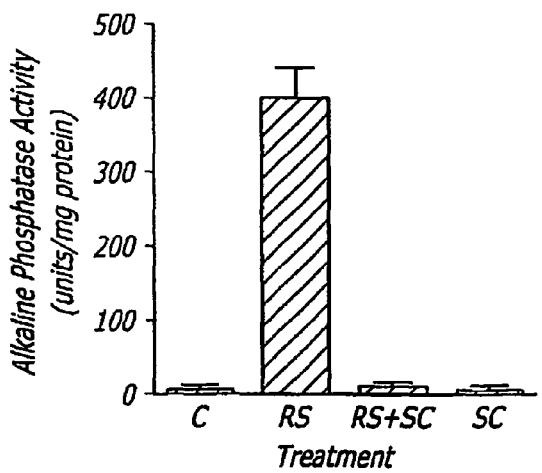
Figure 9B:
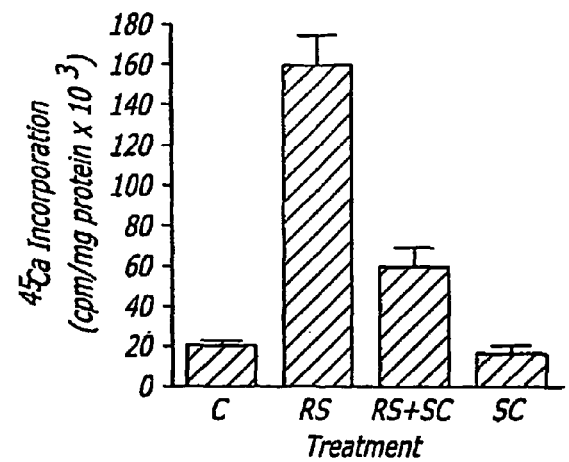
Figure 9D:
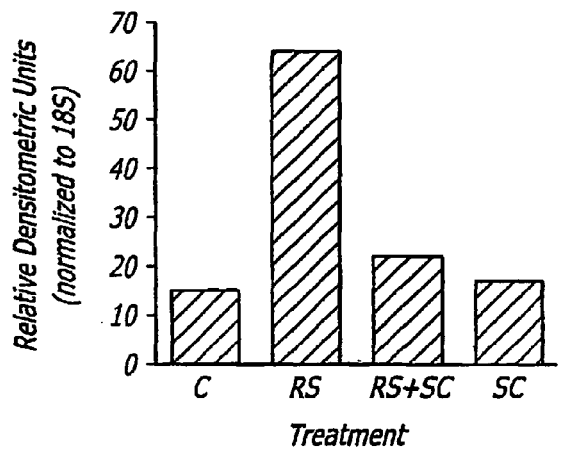
Figure 9E:
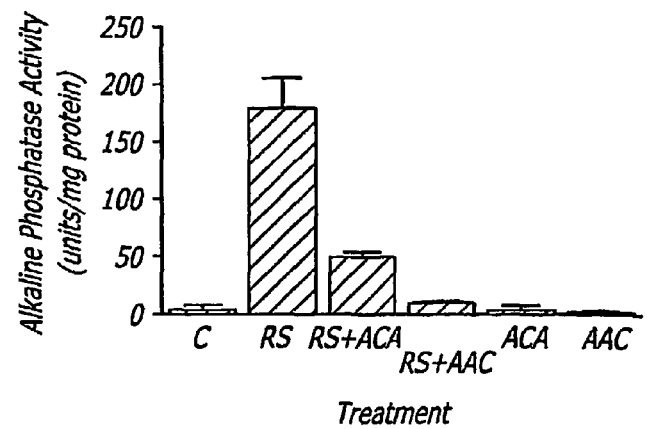
Figure 9F:
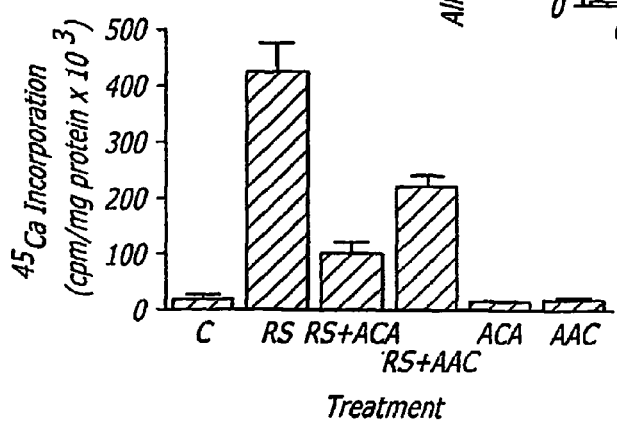

In presence of fetal bovine serum, which corresponds to our experimental conditions, M2 cells in culture express both COX-1 and COX-2 mRNA at all stages of osteogenic differentiation. Consistent with the role of COX in osteogenesis, our studies showed that the COX-1 selective inhibitor SC-560, at 1-20 μM, significantly inhibited the osteogenic effects of the 22R+20S and 22S+20S oxysterol combinations. SC-560 inhibited oxysterol-induced alkaline phosphatase activity (FIG. 9A), mineralization (FIG. 9B), and osteocalcin gene expression (FIGS. 9C and 9D). Although less effective than SC-560, the non-selective COX inhibitors, Ibuprofen and Fluriprofin at non-toxic doses of 1-10 μM, also significantly inhibited the osteogenic effects of 22R+20S oxysterol combination by 25-30%. In contrast, the selective COX-2 inhibitor, NS-398, at the highest non-toxic dose of 20 μM had only negligible inhibitory effects. Furthermore, the osteogenic effects of the oxysterol combination on alkaline phosphatase activity (FIG. 9E) and mineralization (FIG. 9F) were also inhibited by the general phospholipase A2 (PLA2) inhibitor ACA and by the selective cytosolic PLA2 inhibitor, AACOCF3 (AAC). Activation of PLA2 releases arachidonic acid from cellular phospholipids and makes it available for further metabolism by COX enzymes into prostaglandins. Moreover, rescue experiments showed that the effects of the COX-1 and PLA2 inhibitors on oxysterol-induced alkaline phosphatase activity were reversed by the addition of 1 μM PGE2 and 25 μM arachidonic acid, respectively (data not shown). Consistent with previous reports of oxysterol-stimulated metabolism of arachidonic acid, the present results suggest that the osteogenic activity of the oxysterols in MSC are in part mediated by the activation of PLA2-induced arachidonic acid release, and its metabolism into osteogenic prostanoids by the COX pathway.

Example G

Role of ERK in Mediating the Responses of MSC to Oxysterols

The extracellular signal-regulated kinase (ERK) pathway is another major signal transduction pathway previously associated with osteoblastic differentiation of osteoprogenitor cells. Sustained activation of ERKs mediates the osteogenic differentiation of human MSC52, and activation of ERKs in human osteoblastic cells results in upregulation of expression and DNA binding activity of Cbfa1, the master regulator of osteogenic differentiation. Furthermore, ERK activation appears to be essential for growth, differentiation, and proper functioning of human osteoblastic cells.

(A) M2 cells at confluence were pretreated for four hours with RPMI containing 1% FBS, followed by treatment with control vehicle or 5 μM 20S oxysterol for 1, 4, or 8 hours. Next total cell extracts were prepared and analyzed for levels of native or phosphorylated ERK (pERK) using specific antibodies as previously described. Data from a representative of four experiments are shown, each treatment shown in duplicate samples. (B) M2 cells at confluence were pretreated for 2 hours with control vehicle (C) or 20 μM PD98059 (PD) in osteogenic medium as previously described. Next, a combination of 22R and 20S oxysterols (RS, 5 μM each) were added to appropriate wells as indicated. After 10 days of incubation, matrix mineralization was quantified by the $^{45}$Ca incorporation assay as previously described. Data from a representative of three experiments are reported as the mean±SD of quadruplicate determinations, normalized to protein concentration ($p<0.01$ for RS vs. RS+PD). (C) M2 cells at confluence were pretreated for 2 hours with 20 μM PD98059 (PD) in RPMI containing 5% FBS. Next, the cells were treated with control vehicle (C), 10 μM troglitazone (Tro), or 10 μM of 20S or 22S oxysterols, alone or in combination as indicated. After 10 days, adipocytes were visualized by oil Red O staining and quantified by light microscopy as previously described. Data from a representative of three experiments are reported as the mean±SD of quadruplicate determinations.

Figures 10A, 11:
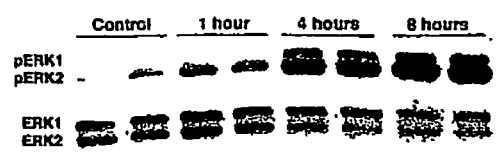
FIG. 11 is a table depicting the effect of 22R+20S oxysterol combination on mouse calvaria bone formation.
Figure 10B:
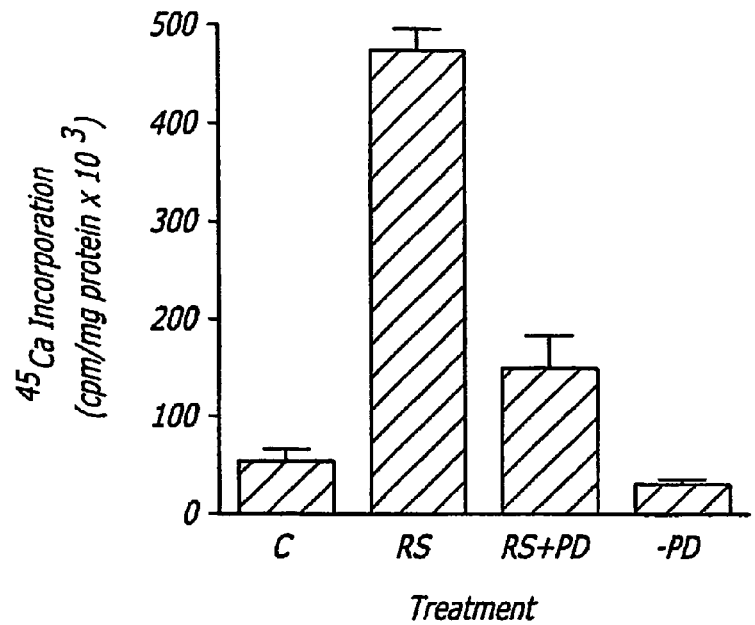
FIG. 10: A) Western blot for pERK or ERK as expressed in M2 cells exposed to control or oxysterol treatment; B) is a bar graph depicting the effect of PD98059 or oxysterol treatment on calcium incorporation in M2 cells; C) is a bar graph depicting the number of adipocytes/field in each treatment group.
Figure 10C:
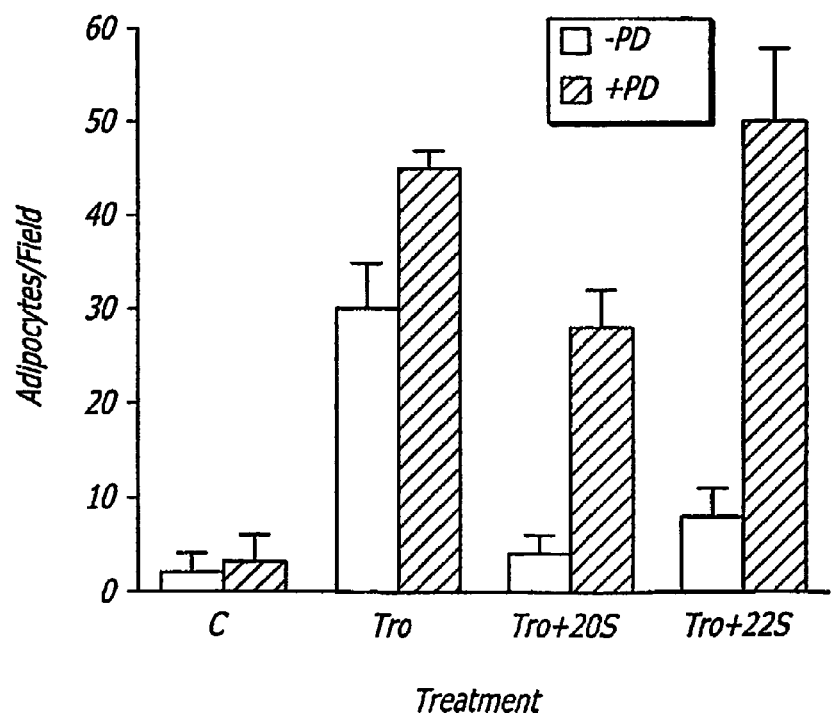

FIG. 10: A) is a Western blot for pERK or ERK as expressed in M2 cells exposed to control or oxysterol treatment; B) is a bar graph depicting the effect of PD98059 or oxysterol treatment on calcium incorporation in M2 cells; C) is a bar graph depicting the number of adipocytes/field in each treatment group Interestingly, the 20S oxysterol used alone or in combination with 22R oxysterol caused a sustained activation of ERK1 and ERK2 in M2 cells (FIG. 10A). Inhibition of ERK pathway by the inhibitor PD98059, inhibited oxysterol-induced mineralization (FIG. 10B) but not alkaline phosphatase activity or osteocalcin mRNA expression in M2 cell cultures (data not shown). These results suggest that sustained activation of ERK is important in regulating certain specific, but not all, osteogenic effects of oxysterols.

Example H

The combination of 20S with either 22R or 22S also produced osteogenic effects in the mouse pluripotent embryonic fibroblast C3H10T1/2 cells, in murine calvarial pre-osteoblastic MC3T3-E1 cells, and in primary mouse MSC as assessed by stimulation of alkaline phosphatase activity and mineralization.

Other combinations of oxysterols that had stimulatory effects on osteogenic activity of marrow stromal cells were 22R+pregnanolone, 20S+pregnanolone, both at 5 μM. Pregnanolone is an activator of another nuclear hormone receptor called PXR. However, the most effective combination oxysterols that consistently induced robust osteogenic activity of the marrow stromal cells including both induction of alkaline phosphatase and mineral formation was 22R- or 22S- in combination with 20S-hydrocholesterols.

Example I

Calvaria from 7 days old CD1 pups were surgically extracted (6 per treatment) and cultured for seven days in BGJ medium containing 2% fetal bovine serum in the presence or absence of 22R+20S (5 μM each). Then, the calvaria were prepared and sectioned. Bone area (BAr) and tissue area (TAr) were determined using digital images of H&E stained parietal bones of the calvarial sections. 8-10 images were captured per calvaria, with each image advanced one field of view along the length of the calvaria until the entire section was imaged. The region of analysis extended from the lateral muscle attachments and included the entire calvarial section except for the saggital suture region, which was excluded. The cross sections of the parietal bones were taken approximately equidistant from the coronal and lambdoid sutures and in the same general region for each individual. Sections of this region were analyzed since they contained little to no suture tissue from the coronal and lambdoid areas. BAr was defined as pink-staining tissue that was not hyper-cellular and displayed a basic lamellar collagen pattern. TAr was defined as the region of tissue between dorsal and ventral layers of lining cells and included BAr as well as undifferentiated cellular tissue and matrix. Separate determinations were made for void area, which was defined as the marrow spaces within the BAr, and was subtracted from BAr measurements prior to calculation of BAr % TAr. To account for differences in TAr between individuals, BAr is reported as a percent of the total TAr measured. Histomorphometric data (continuous variables) were assessed using a one way ANOVA followed by Student's t-test and Dunnett's test vs. control. A p value of 0.05 was used to delineate significant differences between groups. Results are expressed as mean±SD.

Results

Figure 12A:
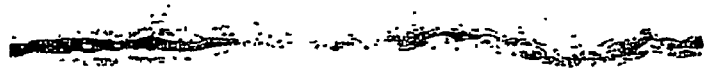
FIG. 12 are representative sections of calvaria treated with a vehicle (A) or 22R+20S oxysterol (B).
Figure 12B:

FIG. 11 is a table depicting the effect of 22R+20S oxysterol combination on mouse calvaria bone formation. A 20% increase in bone formation in the calvaria treated with the combination oxysterols was observed compared to those treated with control vehicle, further supporting the osteogenic activity of the combination oxysterols, ex vivo. FIG. 12 are representative sections of calvaria treated with a vehicle (A) or 22R+20S oxysterol.

I claim:

1. A method of inducing osteoblastic differentiation and inhibiting adipocyte differentiation of mammalian mesenchymal stem cells (MSCs) comprising treating mammalian MSCs with at least one oxysterol,
   wherein the at least one oxysterol is selected from the group consisting of 20S-hydroxycholesterol, 22S-hydroxycholesterol, 22R-hydroxycholesterol and 25-hydroxycholesterol; and
   wherein the MSCs are treated with the at least one oxysterol under conditions that are effective to induce osteoblastic differentiation and to inhibit adipocyte differentiation of the MSC.

2. The method of claim 1, wherein the at least one oxysterol is a combination of oxysterols selected from the group consisting of 20S-hydroxycholesterol and 22R-hydroxycholesterol, and 20S-hydroxycholesterol and 22S-hydroxycholesterol.

3. The method of claim 1, further comprising treating the mammalian MSCs with at least one secondary agent selected from the group consisting of parathyroid hormone, sodium fluoride, insulin-like growth factor I, insulin-like growth factor II and transforming growth factor beta.

4. The method of claim 1, further comprising treating the mammalian MSCs with at least one secondary agent selected from the group consisting of cytochrome P450 inhibitors, phospholipase activators, arachadonic acid, COX enzyme activators, osteogenic prostanoids and ERK activators.

5. A method of stimulating mammalian cells to express a level of a biological marker of osteoblastic differentiation which is greater than the level of a biological marker in untreated cells, comprising exposing a mammalian cell to a selected dose of at least one oxysterol,
   wherein the at least one oxysterol is selected from the group consisting of 20S-hydroxycholesterol, 22S-hydroxycholesterol, 22R-hydroxycholesterol and 25-hydroxycholesterol,
   thereby resulting in a level of expression of a biological marker of osteoblastic differentiation which is greater than the level of a biological marker in untreated cells.

6. The method of claim 5, wherein the at least one oxysterol is a combination of oxysterols selected from the group consisting of 20S-hydroxycholesterol and 22R-hydroxycholesterol, and 20S-hydroxycholesterol and 22S-hydroxycholesterol.

7. The method of claim 5, further comprising treating the mammalian mesenchymal cells with at least one secondary agent selected from the group consisting of parathyroid hormone, sodium fluoride, insulin-like growth factor I, insulin-like growth factor II and transforming growth factor beta.

8. The method of claim 5, further comprising treating the mammalian mesenchymal cells with at least one secondary agent selected from the group consisting of cytochrome P450 inhibitors, phospholipase activators, arachadonic acid, COX enzyme activators, osteogenic prostanoids and ERK activators.

9. The method of claim 5 wherein the biological marker is an increase in at least one of alkaline phosphatase activity, calcium incorporation, mineralization or expression of osteocalcin mRNA.

10. The method of claim 5 wherein the mammalian cells are selected from the group consisting of MSCs, osteoprogenitor cells and calvarial organ cultures.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Mus musculus

```
<400> SEQUENCE: 1
ccagggagaa ccaaagttga                                                    20

<210> SEQ ID NO 2
<211> LENGTH: 21
<212> TYPE: DNA
<213> ORGANISM: Mus musculus

<400> SEQUENCE: 2
cagcactcac ccacttcttt c                                                  21

<210> SEQ ID NO 3
<211> LENGTH: 20
<212> TYPE: DNA
<213> ORGANISM: Mus musculus

<400> SEQUENCE: 3
gaatgaagaa aaccccagca                                                    20

<210> SEQ ID NO 4
<211> LENGTH: 20
<212> TYPE: DNA
<213> ORGANISM: Mus musculus

<400> SEQUENCE: 4
tgggccatta gattcctcac                                                    20
```